(12) United States Patent
Recker et al.

(10) Patent No.: US 8,571,224 B2
(45) Date of Patent: Oct. 29, 2013

(54) SYSTEM FOR ESTIMATING SOUND PRESSURE LEVELS AT THE TYMPANIC MEMBRANE USING PRESSURE-MINIMA BASED DISTANCE

(75) Inventors: Karrie LaRae Recker, Edina, MN (US); Tao Zhang, Eden Prairie, MN (US); Wei Li Lin, Plymouth, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 351 days.

(21) Appl. No.: 12/537,908

(22) Filed: Aug. 7, 2009

(65) Prior Publication Data
US 2010/0260343 A1     Oct. 14, 2010

Related U.S. Application Data

(60) Provisional application No. 61/087,517, filed on Aug. 8, 2008.

(51) Int. Cl.
H04R 29/00 (2006.01)
(52) U.S. Cl.
USPC ............................. 381/56; 381/328; 600/229
(58) Field of Classification Search
USPC ........... 381/312–331, 61, 56–58, 60, 98–109, 381/380, 382; 600/559
See application file for complete search history.

(56) References Cited

U.S. PATENT DOCUMENTS

| | | | |
|---|---|---|---|
| 3,491,214 A | 1/1970 | Rosemond et al. | |
| 4,564,955 A | 1/1986 | Birch et al. | |
| 4,809,708 A * | 3/1989 | Geisler et al. | 600/559 |
| 5,386,475 A | 1/1995 | Birck et al. | |
| 5,699,809 A * | 12/1997 | Combs et al. | 600/558 |
| 5,711,308 A | 1/1998 | Singer | |
| 5,792,073 A | 8/1998 | Keefe | |
| 5,868,682 A * | 2/1999 | Combs et al. | 600/559 |
| 5,897,494 A | 4/1999 | Flock et al. | |

(Continued)

FOREIGN PATENT DOCUMENTS

| | | |
|---|---|---|
| AU | 5830898 A | 9/1998 |
| AU | 2010200103 B2 | 7/2011 |

(Continued)

OTHER PUBLICATIONS

"U.S. Appl. No. 12/130,764, Non-Final Office Action mailed Aug. 20, 2010", 8 pgs.

(Continued)

*Primary Examiner* — Vivian Chin
*Assistant Examiner* — Fatimat O Olaniran
(74) *Attorney, Agent, or Firm* — Schwegman Lundberg & Woessner, P.A.

(57) ABSTRACT

In various embodiments, a system is used to provide an apparatus configured to measure sound in an ear canal of a wearer's ear at a distance from a tympanic membrane of the ear. The sound is measured and received by the apparatus to produce a signal. A frequency analysis is performed on the signal to determine output as a function of the frequency and to determine the frequency of the minima (null). Further, a distance equal to a quarter wavelength of the null frequency is calculated. A correction factor associated with the quarter wavelength is retrieved and applied to the output to generate a corrected output. An estimated sound pressure level at the tympanic membrane from the corrected output is produced.

20 Claims, 22 Drawing Sheets

(56) References Cited

U.S. PATENT DOCUMENTS

| | | | |
|---|---|---|---|
| 5,987,146 | A | 11/1999 | Pluvinage et al. |
| 6,007,494 | A | 12/1999 | Zenner et al. |
| D431,294 | S | 9/2000 | Barnard et al. |
| 6,154,546 | A | 11/2000 | Uvacek |
| 6,674,862 | B1 | 1/2004 | Magilen |
| D506,258 | S | 6/2005 | Nielsen |
| 7,239,711 | B1 | 7/2007 | Andersen et al. |
| 7,599,508 | B1 | 10/2009 | Lynch et al. |
| 7,756,283 | B2 * | 7/2010 | Bramslow ............... 381/318 |
| 7,778,424 | B2 | 8/2010 | Lange |
| 8,059,847 | B2 | 11/2011 | Nordahn |
| 8,315,402 | B2 | 11/2012 | Zhang et al. |
| 2002/0085729 | A1 | 7/2002 | Marx |
| 2004/0028250 | A1 | 2/2004 | Shim |
| 2004/0044389 | A1 | 3/2004 | Crawford |
| 2004/0234094 | A1 | 11/2004 | Saunders et al. |
| 2005/0002539 | A1 | 1/2005 | Nielsen |
| 2006/0045282 | A1 | 3/2006 | Reber |
| 2006/0171550 | A1 | 8/2006 | Bryant et al. |
| 2007/0009107 | A1 | 1/2007 | Lange |
| 2007/0217639 | A1 | 9/2007 | Stirnemann |
| 2008/0152178 | A1 | 6/2008 | Topholm et al. |
| 2008/0194984 | A1 | 8/2008 | Keefe |
| 2008/0260192 | A1 | 10/2008 | Yanz et al. |
| 2008/0260193 | A1 | 10/2008 | Westermann et al. |
| 2008/0298600 | A1 | 12/2008 | Poe et al. |
| 2009/0245525 | A1 | 10/2009 | Zhang et al. |
| 2009/0245560 | A1 | 10/2009 | Zhang et al. |
| 2010/0202642 | A1 | 8/2010 | LoPresti et al. |
| 2010/0246869 | A1 | 9/2010 | Zhang et al. |
| 2011/0098551 | A1 | 4/2011 | Zhang |

FOREIGN PATENT DOCUMENTS

| | | |
|---|---|---|
| AU | 2010201189 | 9/2011 |
| AU | 2009201227 B2 | 10/2011 |
| AU | 2009201228 B2 | 1/2012 |
| DE | 4327634 C1 | 6/1994 |
| EP | 0381608 A2 | 8/1990 |
| EP | 1448014 B1 | 10/2005 |
| EP | 1705950 A2 | 9/2006 |
| EP | 2107831 A2 | 10/2009 |
| EP | 2323553 B1 | 10/2012 |
| WO | WO-8901315 A1 | 2/1989 |
| WO | WO-9931936 A1 | 6/1999 |
| WO | WO-0239784 A1 | 5/2002 |
| WO | WO-2005089016 A1 | 9/2005 |
| WO | WO-2007045254 A1 | 4/2007 |
| WO | WO-2007045271 A1 | 4/2007 |
| WO | WO-2008017326 A1 | 2/2008 |
| WO | WO-2010016925 A1 | 2/2010 |

OTHER PUBLICATIONS

"U.S. Appl. No. 12/130,764, Preliminary Amendment mailed Jul. 21, 2008", 6 pgs.
"U.S. Appl. No. 12/130,764, Response filed Jul. 30, 2010 to Restriction Requirement mailed Jul. 29, 2010", 7 Pgs.
"U.S. Appl. No. 12/130,764, Restriction Requirement mailed Jul. 29, 2010", 9 pgs.
"U.S. Appl. No. 12/980,745, Preliminary Amendment mailed Feb. 14, 2011", 5 pgs.
"International Application Serial No. PCT/US2009/004528, International Preliminary Report on Patentability mailed Feb. 17, 2011", 6 pgs.
"International Application Serial No. PCT/US2009/004528, Search Report mailed Oct. 13, 2009".
"International Application Serial No. PCT/US2009/004528, Written Opinion mailed Oct. 13, 2009".
Chan, C K, et al., "Estimation of Eardrum Acoustic Pressure and of Ear Canal Length From Remote Points in the Canal Length From Remote Points in the Canal", Journal of the Acoustical Society of America, AIP / Acoustical Society of America, Melville, NY, US vol. 87, No. 3, XP009035813 ISSN: 0001-4966 paragraphs [I.D], [II.B], [II.C], [III.B], (Mar. 1, 1990), 1237-1247.
Hudde, H, et al., "Methods for Estimating the sound pressure at the eardrum", Journal of the Acoustical Society of America, AIP / Acoustical Society of America, Melville, NY, US vol. 106, No. 4, XP012001248 ISSN: 0001-4966, (Oct. 1, 2009), 1977-1992.
"U.S. Appl. No. 12/102,602, Final Office Action mailed Aug. 24, 2012", 7 pgs.
"U.S. Appl. No. 12/102,602, Non Final Office Action mailed Apr. 4, 2012", 7 pgs.
"U.S. Appl. No. 12/102,602, Response filed to Restriction Requirement mailed Dec. 8, 2011", 8 pgs.
"U.S. Appl. No. 12/102,602, Response filed Jul. 2, 2012 to Non Final Office Action mailed Apr. 4, 2012", 11 pgs.
"U.S. Appl. No. 12/102,602, Response filed Dec. 26, 2012 to Final Office Action mailed Aug. 24, 2012", 8 pgs.
"U.S. Appl. No. 12/102,602, Restriction Requirement mailed Nov. 8, 2011", 6 pgs.
"U.S. Appl. No. 12/414,876, Non Final Office Action mailed Aug. 12, 2011", 8 pgs.
"U.S. Appl. No. 12/414,876, Notice of Allowance mailed Jan. 12, 2012", 5 pgs.
"U.S. Appl. No. 12/414,876, Notice of Allowance mailed Oct. 11, 2012", 5 pgs.
"U.S. Appl. No. 12/414,876, Response filed Dec. 12, 2011 to Non Final Office Action mailed Aug. 12, 2011", 9 pgs.
"U.S. Appl. No. 12/414,889, Non Final Office Action mailed Dec. 15, 2011", 11 pgs.
"U.S. Appl. No. 12/414,889, Notice of Allowance mailed Jul. 18, 2012", 7 pgs.
"U.S. Appl. No. 12/414,889, Response filed Jun. 14, 2012 to Non Final Office Action mailed Dec. 15, 2011", 9 pgs.
"U.S. Appl. No. 12/685,295 , Response filed Jan. 7, 2013 to Non Final Office Action mailed Nov. 7, 2012", 8 pgs.
"U.S. Appl. No. 12/685,295 , Response filed Aug. 13, 2012 to Non Final Office Action mailed Mar. 12, 2012", 8 pgs.
"U.S. Appl. No. 12/685,295, Final Office Action mailed Nov. 7, 2012", 8 pgs.
"U.S. Appl. No. 12/685,295, Non Final Office Action mailed Mar. 12, 2012", 7 pgs.
"U.S. Appl. No. 12/730,380 , Response filed Jan. 11, 2013 to Final Office Action mailed Oct. 11, 2012", 7 pgs.
"U.S. Appl. No. 12/730,380, Final Office Action mailed Oct. 11, 2012", 10 pgs.
"U.S. Appl. No. 12/730,380, Non Final Office Action mailed Mar. 30, 2012", 10 pgs.
"U.S. Appl. No. 12/730,380, Response filed Aug. 30, 2012 to Non Final Office Action mailed Mar. 30, 2012", 7 pgs.
"Australian Application Serial No. 2009201227, First Examiner Report mailed Apr. 20, 2010", 2 Pgs.
"Australian Application Serial No. 2009201227, Response filed Apr. 18, 2011 to First Examiner Report mailed Apr. 20, 2010", 9 pgs.
"Australian Application Serial No. 2009201228, First Examiner Report mailed Apr. 23, 2010", 1 pg.
"Australian Application Serial No. 2009201228, Office Action Response Filed Aug. 3, 2011", 5 pgs.
"Australian Application Serial No. 2009280002, Office Action Response Filed Sep. 17, 2012", 13.
"Australian Application Serial No. 2010200103, First Examiner Report mailed Feb. 2, 2011", 2 pgs.
"Australian Application Serial No. 2010200103, Response filed Jul. 8, 2011 to First Examiner Report mailed Feb. 2, 2011", 5 pgs.
"Australian Application Serial No. 2010201189, Examiner Report mailed Mar. 11, 2011", 1 pg.
"Australian Application Serial No. 2010201189, Response filed May 19, 2011 to Examiner Report mailed Mar. 11, 2011", 1 pg.
"Australian Application Serial No. 2009201228, Subsequent Examiner Report mailed Jun. 23, 2011", 2 pgs.
"Australian Application Serial No. 2009280002, Office Action Mailed Mar. 23, 2012", 2 Pgs.
"European Application Serial No. 08251441.5, Extended Search Report mailed Dec. 20, 2011", 18 pgs.

(56) References Cited

OTHER PUBLICATIONS

"European Application Serial No. 08251441.5, Response filed Jul. 5, 2012 to Extended Search Report mailed Dec. 20 , 2011", 15 pgs.

"European Application Serial No. 09250957.9, Extended European Search Report mailed Dec. 13, 2010", 5 pgs.

"European Application Serial No. 09250957.9, Response filed Jul. 5, 2011 to Extended European Search Report mailed Dec. 13, 2010", 16 pgs.

"European Application Serial No. 09250958.7, Extended European Search Report mailed Nov. 29, 2010", 5 pgs.

"European Application Serial No. 09250958.7, Response filed Jun. 24, 2011 to Extended European Search Report mailed Nov. 29, 2010", 5 pgs.

"European Application Serial No. 10250039.4, Extended Search Report mailed Apr. 16, 2012", 8 pgs.

"European Application Serial No. 10250039.4, Response filed Nov. 16, 2012 to Extended Search Report mailed Apr. 16, 2012", 10 pgs.

"European Application Serial No. 10250568.2, Extended Search Report mailed Dec. 13, 2011", 8 pgs.

"European Application Serial No. 10250568.2, Office Action mailed Jan. 16, 2012", 2 pgs.

"European Application Serial No. 10250568.2, Response filed Jul. 10, 2012 to Extended Search Report mailed Dec. 13, 2011", 11 pgs.

"European Application Serial No. 08251441.5, Partial European Search Report mailed Jul. 14, 2011", 5 pgs.

Dillon, Ph.D., Harvey, "Hearing Aids", 4.4 Practical Issues in Real-Ear Testing, (Jan. 1, 2001), 101-104.

Moodie, K Shane, et al., "Procedure for Predicting Real-Ear Hearing Aid Performance in Young Children", Am. Journal of Audiology, Am. Speech-Language-Hearing Association, 3(1), (Mar. 1, 1994), 23-31.

Munro, Kevin J, et al., "Measuring the Real-Ear to Coupler Difference Transfer Function with and Insert Earphone and a Hearing Instrument: Are they the same?", Ear and Hearing, 26(1), (Feb. 1, 2005), 27-34.

Pascal, Jerome, et al., "Linear and nonlinear model of the human middle ear", J. Acoust. Soc. Am., vol. 104, No. 3, Pt. 1, (Sep. 1998), 1509-1516.

Yanz, Jerry, et al., "Real Ear Measurement System Using Thin Tube", U.S. Appl. No. 60/912,343, filed Apr. 17, 2007, 19 pgs.

\* cited by examiner

| DISTANCE (mm) | 1000 Hz NO CF | 1000 Hz W/CF | 2000 Hz NO CF | 2000 Hz W/CF | 3000 Hz NO CF | 3000 Hz W/CF | 4000 Hz NO CF | 4000 Hz W/CF | 5000 Hz NO CF | 5000 Hz W/CF | 6000 Hz NO CF | 6000 Hz W/CF | 7000 Hz NO CF | 7000 Hz W/CF | 8000 Hz NO CF | 8000 Hz W/CF |
|---|---|---|---|---|---|---|---|---|---|---|---|---|---|---|---|---|
| 6 | .4 | .3 | .4 | .4 | .5 | .2 | .9 | .2 | 1.1 | .4 | 2.0 | .5 | 2.5 | .7 | 3.6 | .9 |
| 8 | .3 | .3 | .5 | .5 | .8 | .2 | 1.1 | .3 | 1.7 | .4 | 3.0 | .6 | 4.3 | 1.1 | 6.1 | 1.3 |
| 10 | .4 | .4 | .7 | .5 | 1.2 | .3 | 1.9 | .5 | 3.1 | .7 | 6.1 | .8 | 9.8 | 1.6 | 12.2 | 1.8 |
| 12 | .5 | .4 | .8 | .6 | 1.9 | .2 | 2.8 | .5 | 4.8 | .7 | 8.8 | 1.7 | 13.6 | 3.1 | 12.4 | 2.1 |
| 14 | .5 | .5 | 1.2 | .4 | 2.2 | .4 | 3.7 | .7 | 7.2 | .9 | 12.6 | 1.7 | 11.5 | 1.6 | 9.7 | 2.0 |
| 16 | .5 | .7 | 1.4 | .5 | 2.9 | .3 | 4.5 | .7 | 8.4 | 1.2 | 14.5 | 1.3 | 13.4 | 2.3 | 7.6 | 1.9 |

| DISTANCE (mm) | 9000 Hz NO CF | 9000 Hz W/CF | 10000 Hz NO CF | 10000 Hz W/CF | 11000 Hz NO CF | 11000 Hz W/CF | 12000 Hz NO CF | 12000 Hz W/CF | 13000 Hz NO CF | 13000 Hz W/CF | 14000 Hz NO CF | 14000 Hz W/CF | 15000 Hz NO CF | 15000 Hz W/CF | 16000 Hz NO CF | 16000 Hz W/CF |
|---|---|---|---|---|---|---|---|---|---|---|---|---|---|---|---|---|
| 6 | 7.3 | 1.3 | 8.2 | 1.3 | 7.8 | 1.4 | 9.2 | 2.3 | 10.6 | 3.8 | 12.0 | 4.2 | 8.7 | 5.7 | 9.0 | 6.1 |
| 8 | 9.9 | 1.8 | 9.9 | 1.9 | 12.2 | 1.8 | 9.8 | 2.4 | 10.1 | 2.8 | 7.8 | 3.1 | 6.8 | 4.7 | 4.7 | 5.5 |
| 10 | 16.2 | 1.0 | 11.0 | 1.8 | 7.2 | 1.9 | 6.8 | 3.5 | 5.1 | 4.0 | 4.0 | 4.8 | 3.1 | 4.9 | 2.7 | 6.3 |
| 12 | 10.5 | 1.7 | 7.0 | 1.5 | 5.5 | 2.5 | 4.1 | 3.7 | 3.8 | 4.0 | 3.6 | 4.9 | 4.1 | 5.3 | 4.7 | 8.2 |
| 14 | 8.3 | 1.6 | 4.7 | 2.9 | 4.4 | 2.4 | 3.8 | 3.2 | 3.5 | 5.2 | 3.9 | 3.3 | 4.9 | 5.5 | 5.0 | 9.8 |
| 16 | 5.6 | 2.3 | 3.5 | 3.0 | 3.5 | 3.5 | 4.5 | 4.7 | 5.1 | 4.1 | 4.9 | 3.5 | 9.8 | 7.6 | 9.4 | 8.0 |

SYSTEM FOR ESTIMATING SOUND PRESSURE LEVELS AT THE TYMPANIC MEMBRANE USING PRESSURE-MINIMA BASED DISTANCE

CROSS REFERENCE TO RELATED APPLICATION(S)

This application claims the priority of U.S. Provisional Application No. 61/087,517, entitled "SYSTEM FOR ESTIMATING SOUND PRESSURE LEVELS AT THE TYMPANIC MEMBRANE USING PRESSURE-MINIMA BASED DISTANCE", filed Aug. 8, 2008, which is hereby incorporated by reference in its entirety.

FIELD OF THE INVENTION

The present application relates generally to measurement of sound pressure levels near a tympanic membrane and in particular to method and apparatus for estimating sound pressure levels using measurements away from the tympanic membrane.

BACKGROUND

Hearing assistance devices, such as hearing aids, are designed to provide signal processing that assists the hearing of a wearer. In the case of hearing aids, the wearer typically has hearing loss which is characterized by an audiogram which shows where such loss occurs as a function of frequency and the extent of the hearing loss. Hearing aids provide, among other things, customizable gain as a function of frequency to compensate for that hearing loss. The process of customizing a hearing aid to restore hearing to a more natural level is called "fitting." One way to determine if the appropriate settings are employed in the fitting process is to monitor the sound pressure level (SPL) at or near the tympanic membrane and discomfort of the individual of the wearer to determine that the proper gain has been applied to the wearer of the device. Such measurements can present a danger of damage to the tympanic membrane if not properly performed. These measurements may also require complicated microphone measurements within the patient's ear canal that are prone to error. Such methods can distort the natural soundfield present in the ear canal or interfere with the normal operation of the hearing aid during test, especially at higher frequencies of the hearing spectrum.

Recently, researchers have given much attention to determining whether individuals with hearing loss can benefit from extended high-frequency information. While some of these studies have shown improved sound quality or speech understanding by increasing the bandwidth beyond 6 kHz, there remain several challenges that must be overcome before extended bandwidth hearing aids can become a clinical reality.

Thus, there is a need in the art for improved measurements of sound pressure level. Such measurements should be accurate at high frequencies and should be straightforward to perform for accurate measurement of sound pressure level near the tympanic membrane.

SUMMARY

In various embodiments a method is implemented to provide an apparatus configured to measure sound in an ear canal of a wearer's ear at a distance from a tympanic membrane of the ear. The sound is measured and received by the apparatus to produce a signal. A frequency analysis is performed on the signal to determine the output as a function of the frequency and to determine the frequency of the minima (null). Further, a distance equal to a quarter wavelength of the null frequency is calculated. A correction factor associated with the quarter wavelength is retrieved and applied to the output to generate a corrected output. An estimated sound pressure level at the tympanic membrane from the corrected output is produced.

In variations of the embodiment, a fast Fourier transform (FFT) is performed on the signal. Also, the correction factor may be a function of the width or depth of the minima. In various embodiments a complex tone is generated for sound measurement by the apparatus. The complex tone may include frequencies separated by 50 Hz and ranging from 100 Hz to 16000 Hz. In some embodiments a swept tone is generated for sound measurement by the apparatus. Additionally, the estimated sound pressure level at the tympanic membrane from the corrected output may be displayed on a display device.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 15 is a table of median absolute errors for distances from the TM according to an embodiment of the present subject matter.

FIG. 16 is table of transfer functions at estimated distances from the TM according to an embodiment of the present subject matter.

DETAILED DESCRIPTION

Figure 1:
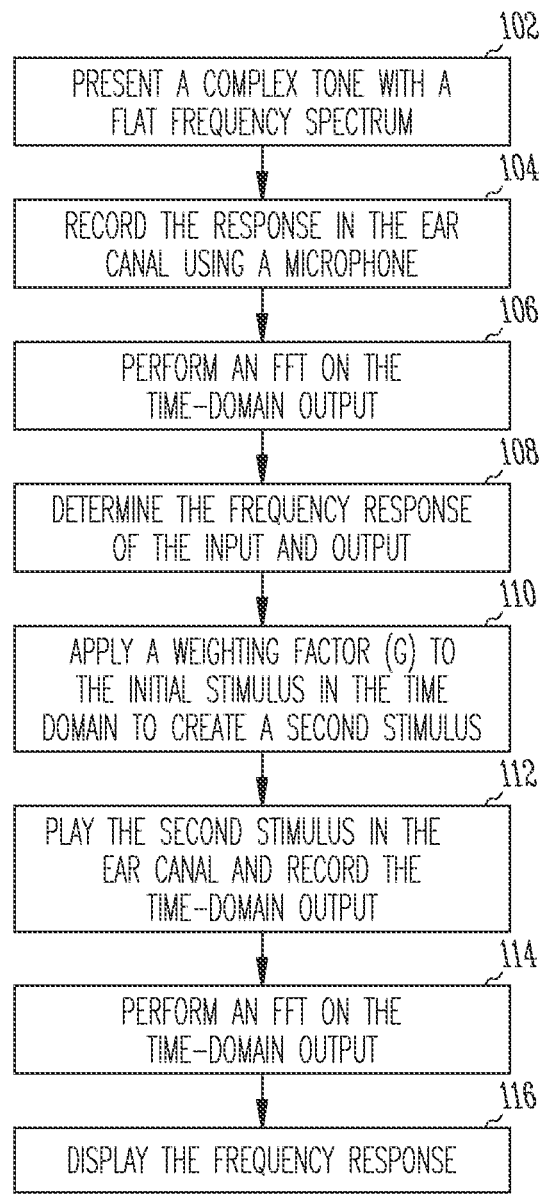
FIG. 1 is an example method according to an embodiment of the present subject matter.

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Among other things, the present subject matter provides a method to improve the accuracy of estimated high-frequency sound pressure level (SPL) at the tympanic membrane (TM). In an embodiment, an in-ear monitor was used to present a stimulus with frequency components up to 16 kHz. Responses were measured along the ear canal in 2 mm increments. Average correction factors were generated based on the distance to the TM as determined by the dominant pressure-minima. Adding these correction factors improved the estimated SPL at the TM through 9-15 kHz, depending on the measurement location, with typical improvements of 16-22 dB at the frequency of the dominant pressure minima.

Introduction

Recently, researchers have given much attention to determining whether individuals with hearing loss can benefit from extended high-frequency information. While some of these studies have shown improved sound quality or speech understanding by increasing the bandwidth beyond 6 kHz, there remain several challenges that must be overcome before extended bandwidth hearing aids can become a clinical reality. Indeed, even if suitable devices and appropriate prescriptive gain targets were readily available, there would still remain the challenge of verifying the hearing aid fitting. While real-ear measurements are considered best practice for ensuring audibility, currently available commercial real-ear equipment is typically capable of measuring up to 8 kHz. And, even if commercial systems were readily capable of measuring higher frequencies, it is a challenge to use past measurement methods and apparatus to safely and accurately make these measurements. This application describes how to make and use a system to improve the estimated sound pressure level (SPL) at the tympanic membrane (TM), over a wide frequency range using measurements made a distance from the TM.

To determine the SPL estimate at the TM, making measurements right next to the TM using standard probe microphone real-ear equipment may lead to safety and discomfort concerns. The present subject matter provides a system for measurements performed at locations away from the TM. For example, in various embodiments the measurements are made within 5 mm of the TM, and the SPL at the TM is estimated based on these measurements. In past approaches, reasonably accurate estimates of SPL at the TM are possible for frequencies below 3 kHz, where the ear canal can be approximated by a cylindrical tube with a perpendicular termination. For frequencies above 3 kHz, multiple factors come into play, which can cause the SPL away from the TM to differ significantly from that at the TM.

For example, standing waves are a major contributor to these differences. Standing waves occur because there is an acoustic impedance mismatch between the air in the ear canal and the TM, which causes some of the sound to be reflected off the TM, and back into the ear canal. The reflected sound interacts with the incident sound to produce standing waves in the ear canal. Most frequently, the standing waves cause the levels in the ear canal to be lower than those at the TM, with the minimum occurring at a location in the ear canal that corresponds roughly to the ¼ wavelength of a particular frequency. These pressure minima are location-dependant and will gradually shift lower in frequency the farther the measurement from the TM. Lower frequencies (e.g. 2 kHz) will be relatively unaffected by standing waves, as their ¼ wavelengths (43 mm in this example) occur at distances that are outside the average ear canal length of 25 mm. Also, because of the relationship between the measurement location and the frequency of the dominant pressure minima, the dominant pressure minima can provide a reasonable estimate of the distance to the TM.

In addition to standing waves, differences in individual ear canal geometry and TM impedance will alter the measured response by affecting the frequency and the depth of the pressure minima Differences across ear canals can cause variations of 20 dB or more in SPL above 8 kHz. Additionally, differences in TM impedance can shift the frequency of the dominant pressure minima by up to 3 mm in the 5-9 kHz range. Collectively, these differences make it difficult to predict the SPL at the TM based on measurements away from the TM, for an individual, in the high frequencies.

The SPL could be estimated by modeling the properties of the ear. However, because models are often based on the average ear, SPL estimates could be inaccurate for a given individual. To customize the model for an individual, detailed information about the particular ear (e.g. its geometry, TM impedance, middle ear characteristics, etc.), is often required.

As an alternative to SPL measurements, some researchers have successfully used intensity measurements to estimate the levels at the TM. These measurements can avoid the problems of standing waves by separating the incident (forward moving) intensity from the reflecting intensity. However, these measurements may not be well accepted by clinical practitioners, who may be less familiar with intensity measurements than SPL measurements.

In an embodiment, a method is used to improve the estimated SPLs at the TM by adding average correction factors to measured responses in the ear canal. This technique provides several advantages over the methods previously mentioned. For example, the frequency of the dominant pressure minima is the only information that must be known in order to implement it.

In one embodiment, the technique focuses on the extended high frequencies, up to 16 kHz. As an initial step in the experiment, a real-ear measurement system capable of generating and recording accurate responses in the ear canal, into the extended high frequencies, was created. Further, the repeatability and reproducibility of the measurements, within and across individuals, at various locations along the ear canal was examined.

Methods

Participants

In one study, two groups of 10 adults participated in the study. The first, the "reference" group, included 9 males and 1 female, 22-50 years old (median 34). The second group, the "verification" group, included 2 males and 8 females, 25-81 years old (median 39). All participants had normal middle ear function, as determined by pure-tone air and bone conduction testing, performed with a GSI 61 audiometer, and tympanometry, performed with an AT235h impedance audiometer. Individuals with excessive ear wax were not used, because ear impressions were taken on all participants.

Measurements were made on one ear per participant. In both groups, measurements were made on an equal number of right and left ears. However, a few unplanned differences existed between the two groups. The reference group was primarily males and the verification group was primarily females. Additionally, on average, the reference group was younger than the verification group. Lastly, all of the measurements on the reference group were performed by a single experimenter, at one site, whereas measurements for 8 of the 10 participants in the verification group were performed by a second experimenter. Measurements on 7 of these individuals were performed at a second site.

Equipment/Set-Up

FIG. 1 illustrates an example method of demonstrating the present subject matter. At block 102, a custom application was created in Matlab to generate a sound source that was sent from a Dell Optiplex GX620 computer to a Gina echo soundcard and then routed to a pair of custom in-ear monitors (IEMs) via audio cables. At block 104, the response (e.g., a signal produced) was recorded in the ear canal using an ER-7C microphone, and routed back to the computer for storage and offline frequency analysis.

The stimulus presentation method was chosen after performing several piloting experiments examining stimulus level (85/90 dB SPL), stimulus shaping (flat/spectrally-shaped) and stimulus resolution (5/10/50/100 Hz). In various embodiments, the tone is a sweep of frequencies (e.g., 20-20000 Hz). In one embodiment, a tone complex with energy at 50 Hz intervals, from 100-16000 Hz is used. Other tones, tone complexes, and approaches may be used without departing from the scope of the present subject matter.

The initial stimulus had a flat spectrum and was presented for 3 seconds at ~90 dB SPL at the TM. At block 106, a Fast Fourier Transform (FFT) was performed on the time-domain output of the recorded response to determine the frequencies at which the response was close to the noise floor. At block 108, the difference in the frequency response of the input and the output (H) was determined. At block 110, a weighting factor (G) was applied to the initial stimulus in the time domain to create a second stimulus: $G=10^{\wedge}(H/20)$; H was limited by $[-30, 30]$ dB. The weighting factor shaped the stimulus to boost the level at the frequencies that were close to the noise floor. At block 112, the second stimulus was played through the in-ear monitor, and the time-domain output was recorded. At block 114, an FFT was performed on the output and at block 116 the frequency response was displayed on the experimenter's computer monitor and stored for offline analysis.

A few differences existed in the test set-up between the reference group and the verification group. First, all IEMs should have been wired with Hi-Fi, transducers—a Knowles TWFK (part #30017-000), which consists of a FK woofer and a wideband FK tweeter. However, due to a wiring error, only the devices for the verification group were wired with both transducers. However, additional measurements with the single transducer devices showed that they operated linearly across frequency, and that they had sufficient signal-to-noise ratios. Second, the IEMs for the initial group had two vents, one just large enough to insert a probe tube, and the other a 3 mm vent, which remained open during the testing. For all but one pair of devices in the verification group, there was only a probe-tube vent. The venting would have affected the individual responses, however, because venting effects are constant throughout the ear canal, these effects would have canceled out when two responses were normalized to each other, as occurred with our technique.

Real Ear Measurements (REM)

In an embodiment, to minimize the potential for discomfort, we attached nylon fibers to the ends of the probe tubes, so that they extended 2 mm beyond the tips of the tubes. The probe tubes were routed through the vents of the IEMs until participants reported that they could hear or feel the fibers on their TMs. Some individuals reported a scratching sound, while others reported a pressure sensation or a slight discomfort. This technique has been used successfully by other experimenters, although, due to safety and discomfort concerns, it is not recommended for clinical applications.

To verify the results, tests were performed where the fibers are not used, and the initial measurements were made at the TM. These measurements were used to estimate the accuracy of the initial 2 mm placement relative to the TM response.

At the initial probe-tube placement, three measurements were made, and the probe tube was marked at the faceplate using a permanent marker. The probe tube was then pulled out of the ear canal by 2 mm, as determined by measuring the distance between the mark on the probe tube and the faceplate of the IEM. At that location, another three measurements were made. This process continued, with 3 measurements at each location along the ear canal, in 2 mm increments, until the probe tube was 16 mm from the TM. At that point, the IEM and the probe tube were removed from the ear canal, reinserted, and another set of measurements was performed. In all, three sets of measurements were made on each ear in the same session.

Based on the high degree of repeatability for the three successive measurements at each location along the ear canal for the reference group, only a single measurement was made at each location along the ear canal for the verification group.

Correction Factors

In one embodiment for each individual three sets of measurements were made at each location along the ear canal, with the probe tube and the IEM removed between sets. Variations in probe tube placement caused variations in the measured frequency responses. Generally, the amplitude of the response was higher, especially in the very high frequencies, the closer the measurement to the TM. Therefore, for each individual, the 2-mm measurement with the highest amplitude in the high frequencies served as the estimated SPL at the TM.

Figure 2:
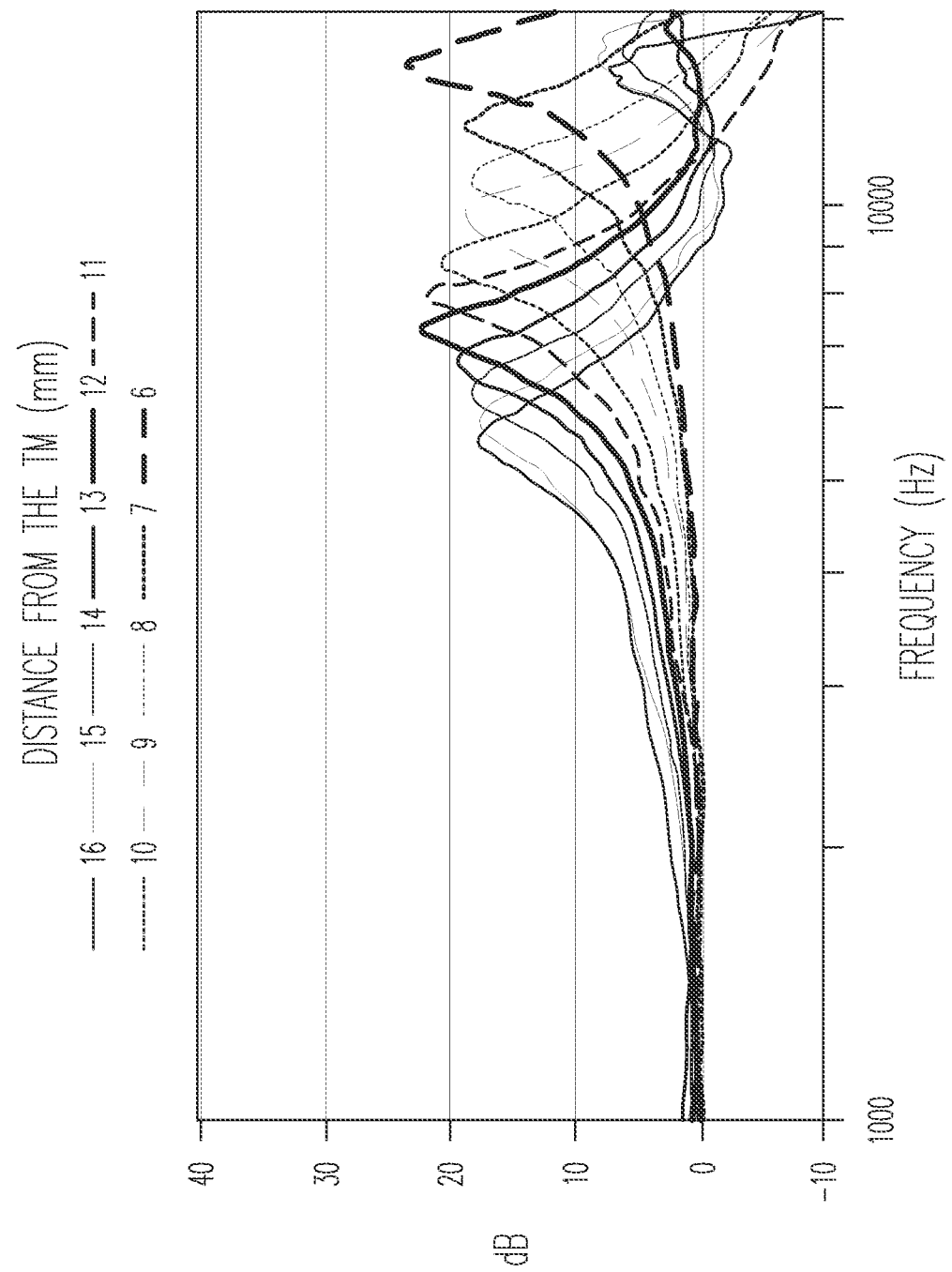
FIG. 2 illustrates correction factors for pressure-minima-based distances of 6-16 mm from the TM according to an embodiment of the present subject matter.

By normalizing each participant's responses along the ear canal to his/her best 2 mm response (e.g., finding the difference between the two responses), we were able to determine the frequency of the dominant pressure minima, and therefore estimate the distance to the TM based on the ¼ wavelength of that frequency. In an embodiment, because the normalized responses also provided an estimate of the error, at that location in the ear canal, correction factors were generated by grouping them according to their estimated distances from the TM and averaging them. Correction factors were generated for distances of 6 to 16 mm from the TM, in 1 mm increments (e.g. 12 mm±0.5 mm as illustrated in FIG. 2. In an embodiment to verify this technique, the estimated distance to the TM for each measurement along the ear canal was determined, the appropriate correction factor was added to the output, and the estimated response was compared to that individual's measured response 2 mm from the TM.

The correction factors were not based on the measured distance to the TM, which would not have worked well for two reasons. First, there is not a quick, accurate, easy, and noninvasive way in which to measure the distance from the TM. Second, the frequency of the dominant pressure minima can vary greatly from person to person, even at the same distance from the TM, mostly due to the differences in geometry and acoustic impedance of each individual ear. As a result, average correction factors based on the measured distance would have large standard deviations, and using them would likely result in error as often as they would be helpful.

Results

Repeatability/Reproducibility

In some embodiments, at a single location in the ear canal, successive measurements (with no changes to the set-up) were highly repeatable. On average, they were within 3 dB of each other, through 16 kHz, at all locations along the ear canal. Additionally, 90% of measurements were repeatable within 3 dB through 8 kHz and 6 dB through 15,950 Hz. Repeatability tended to be poorer, especially above 10 kHz, and at greater distances from the TM.

Figure 3A:
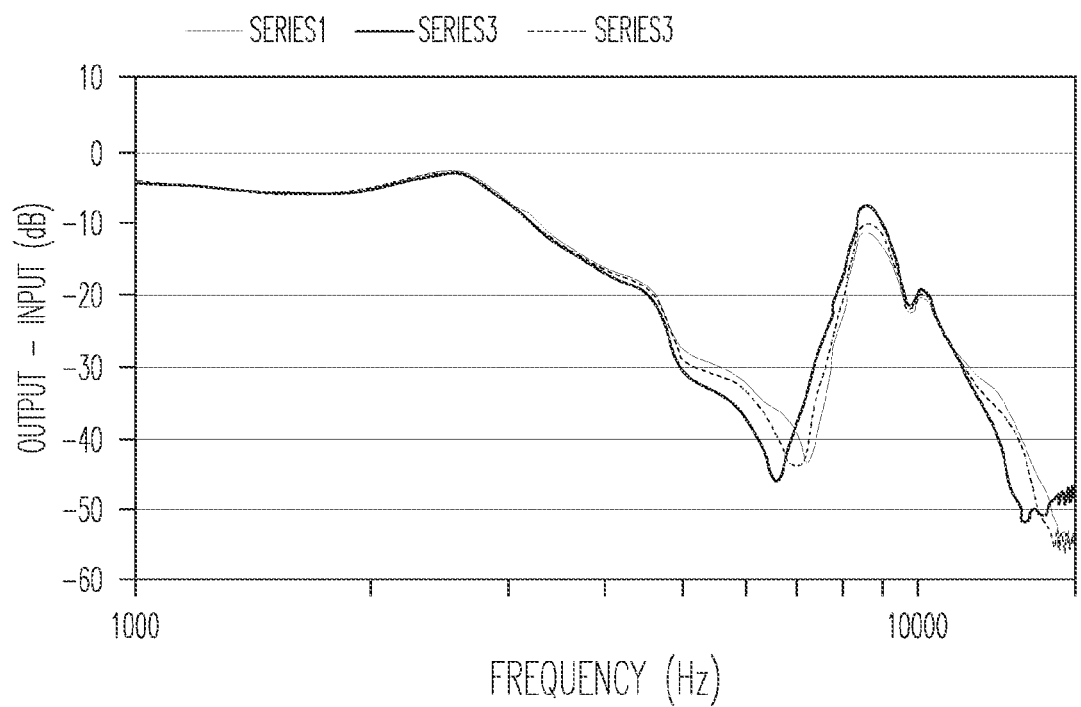
FIGS. 3A-3B illustrate reproducibility at 16 mm from the TM according to an embodiment of the present subject matter.
Figure 3B:
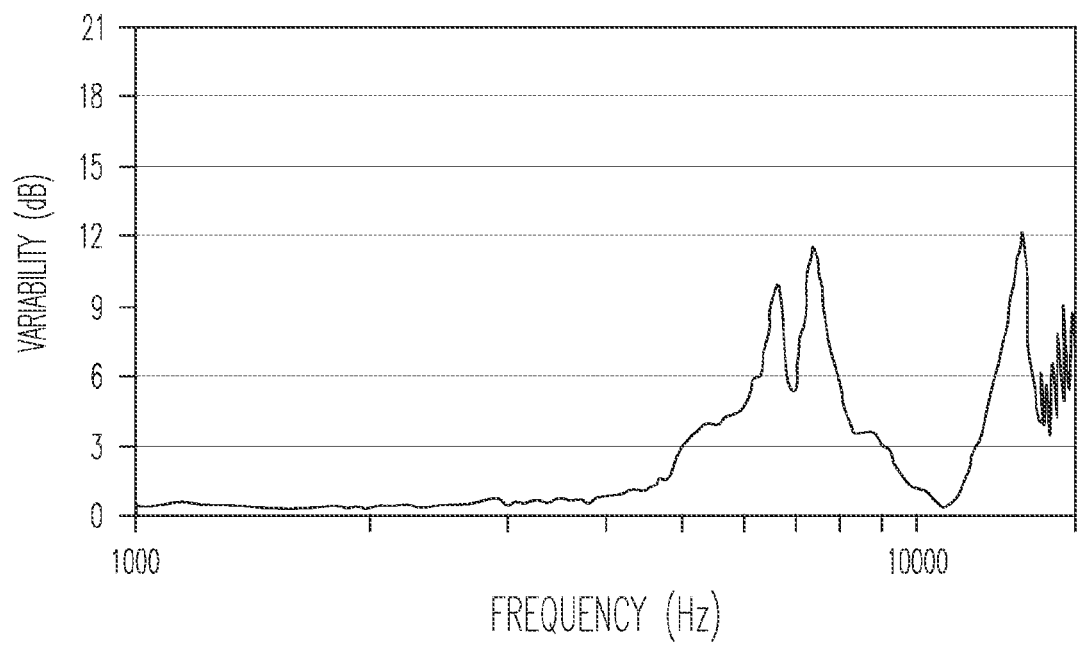
Figure 4A:
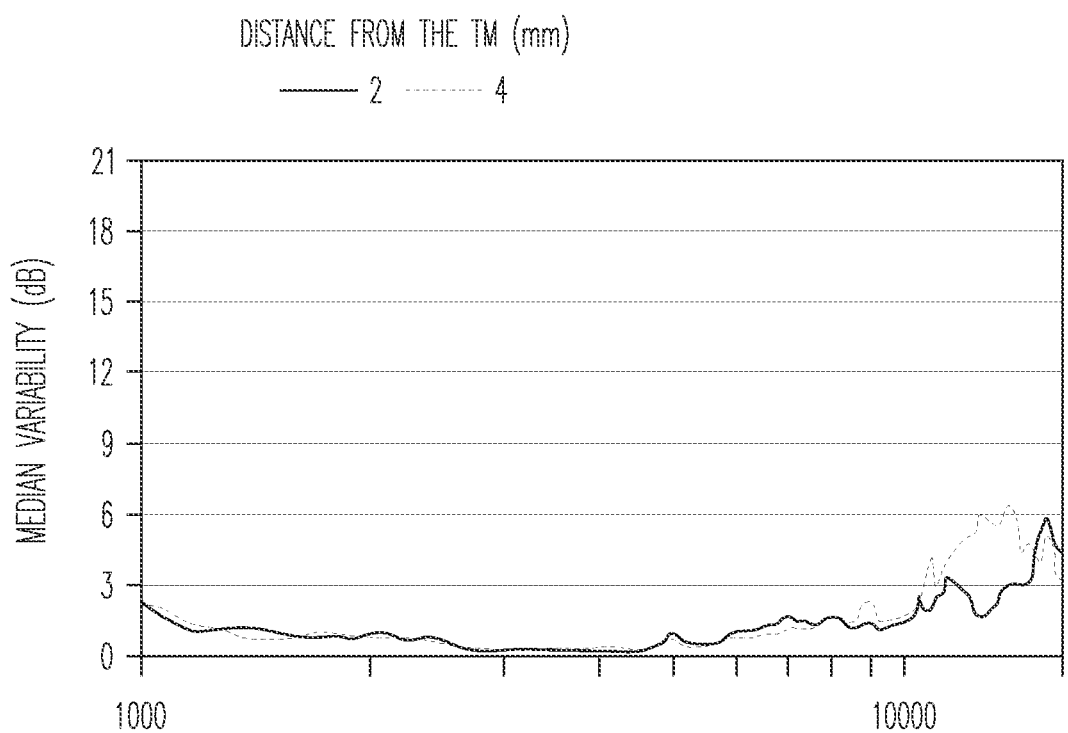
FIGS. 4A-4F illustrate variability in measurements according to an embodiment of the present subject matter.
Figure 4B:
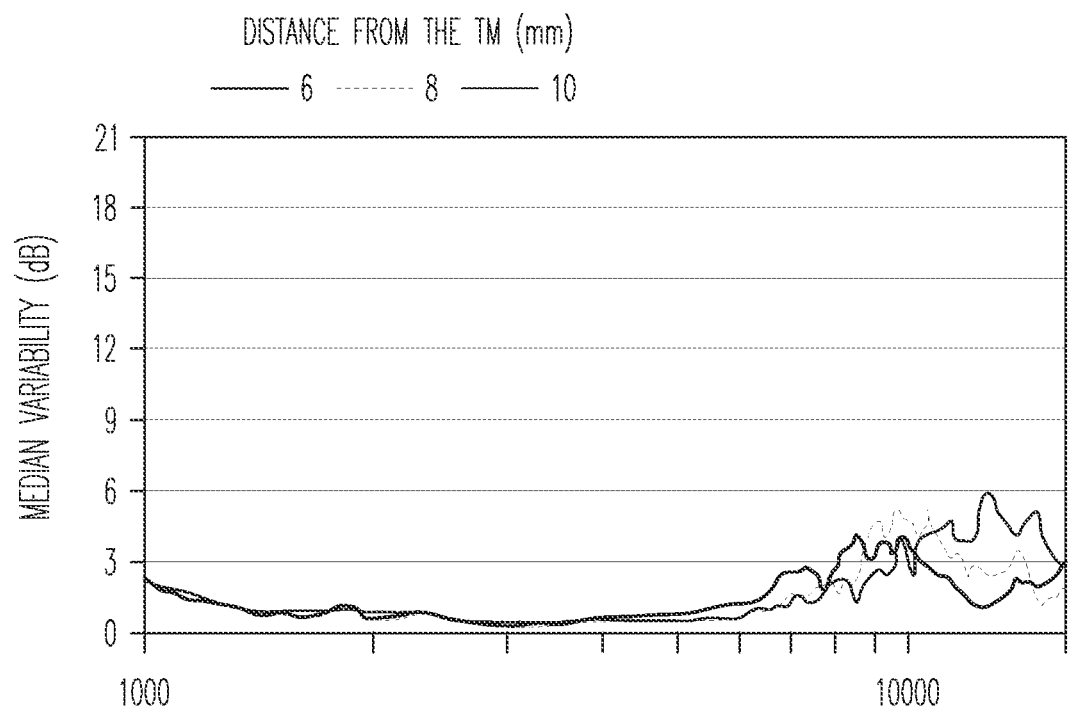
Figure 4C:
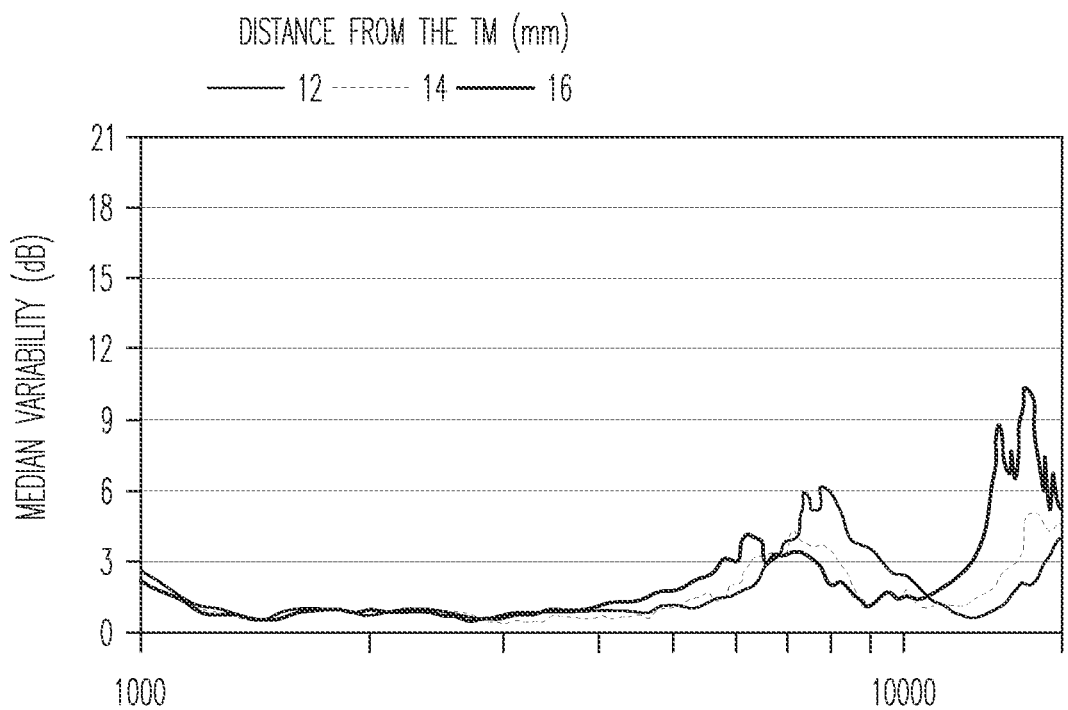
Figure 4D:
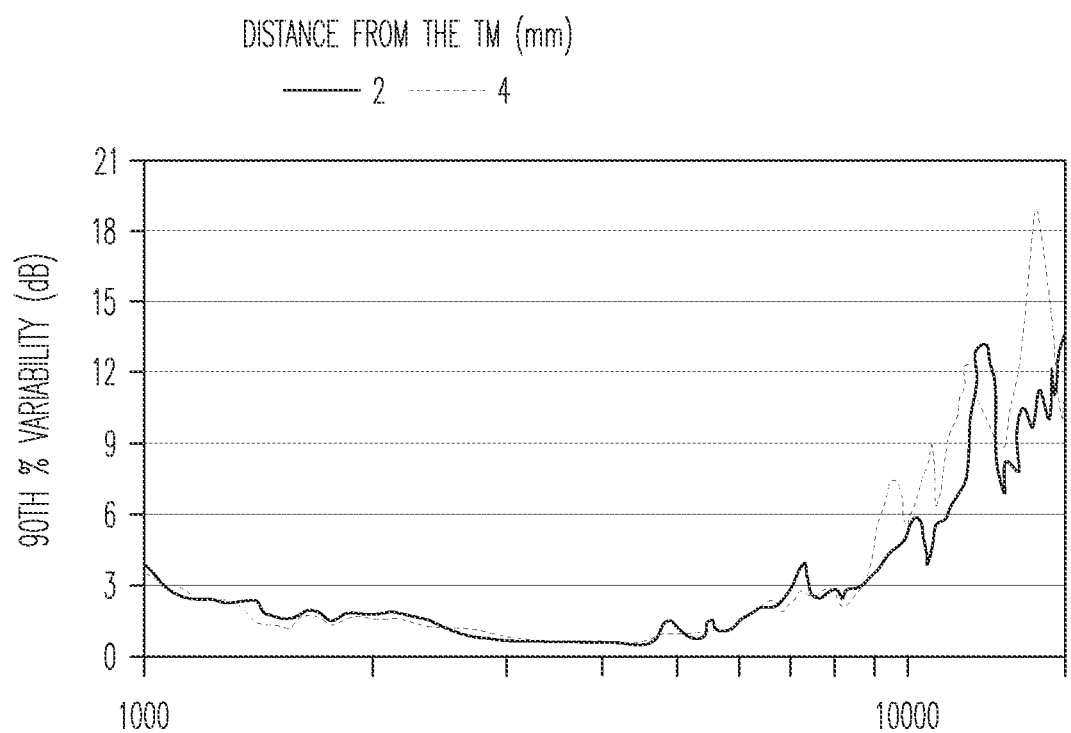
Figure 4E:
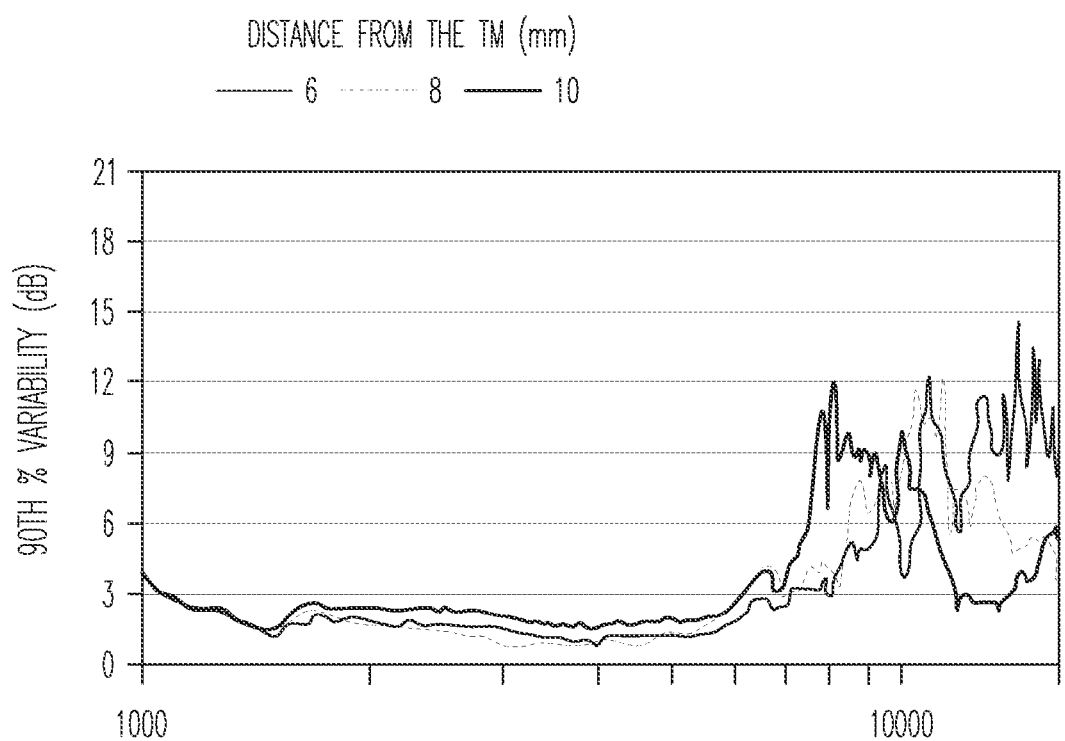
Figure 4F:
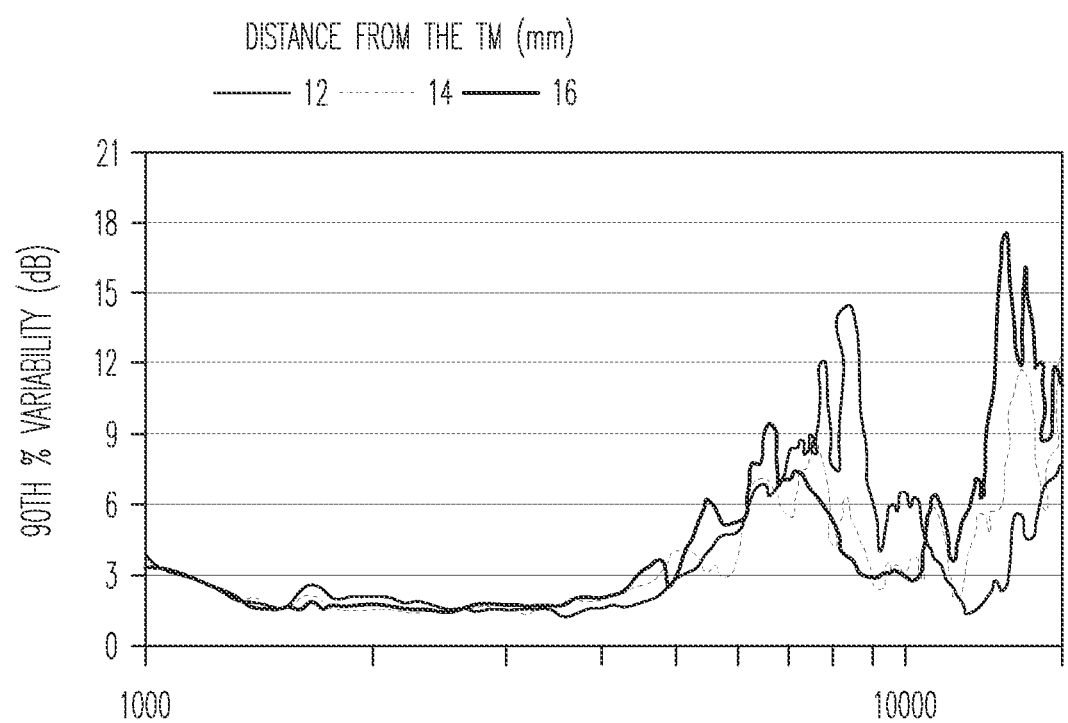

In some embodiments, reproducibility (when the probe tube and the IEMs were removed from the ear, reinserted, and the measurements were repeated) was not as consistent. FIGS. 3A and 3B depict graphs which shows the three measured responses (output) for one individual at 16 mm from the TM, and demonstrates the typical results of poorer reproducibility around the pressure minima (in this case ~7 kHz) and in the high frequencies. In this example, the levels differed by up to 12.4 dB across measurements.

FIGS. 4A-4F depict graphs of variability data for the group. Data are plotted on different graphs, based on the measured distance to the TM. Median and 90$^{th}$ percentile data are plotted separately. Median values were within 3 dB through 5700 Hz and (generally) 6 dB through 13 kHz. Ninety percent of values were within 3 dB through 4400 Hz, 6 dB through 5400 Hz and 9 dB through 6450 Hz. This highlights the fact that, while on average the results were highly reproducible, outliers existed for whom reproducibility was much poorer. Reproducibility was also poorer the greater the measurement distance from the TM.

Figure 5:
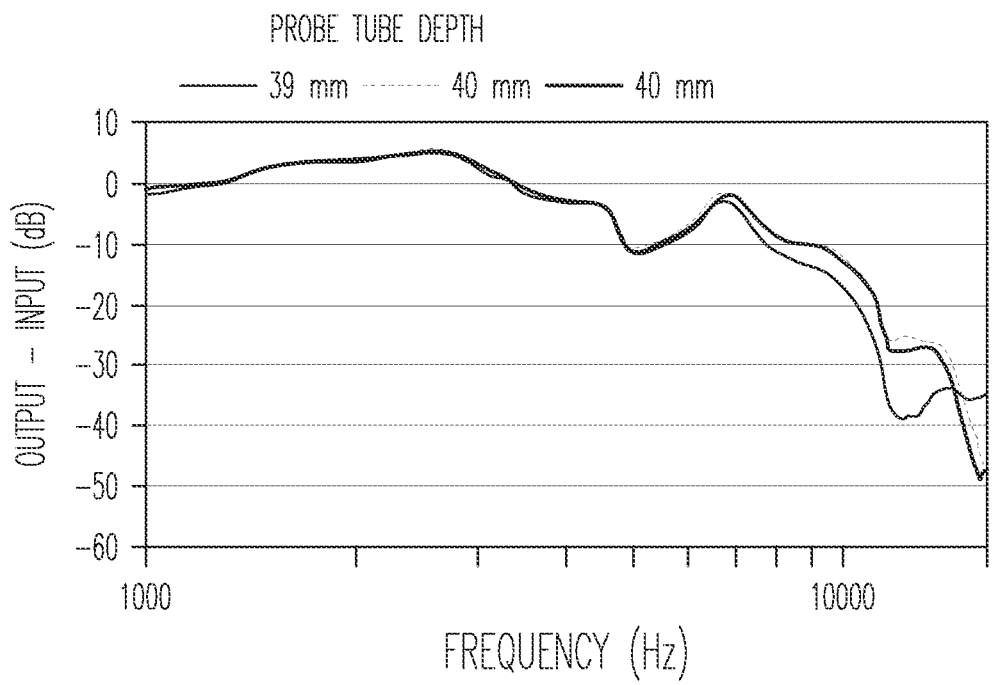
FIG. 5 illustrates real-ear responses according to an embodiment of the present subject matter.

In various embodiments, variations in probe tube placement as small as 1 mm significantly reduced the reproducibility, especially in the high frequencies. As an example, FIG. 5 shows three responses for one individual at the location in his ear canal at which he reported that the fibers were at his TM. Note, for 2 of the 3 measurements, this occurred at a probe tube depth of 40 mm, and for one measurement it occurred at a depth of 39 mm. For the two measurements at 40 mm, the reproducibility was very good, within 3 dB through 14550 Hz, whereas the measurement at 39 mm was within 3 dB of the other two responses only through 8700 Hz; around 12 kHz the response differed from the other two by more than 10 dB.

In an embodiment, the initial probe tube placement was not verified objectively, it was based on participants' reports— when they heard or felt the fibers at their TMs, and it varied for 5 of the 10 individuals, by up to 2 mm, across sets of measurements. This may have occurred because participants were unreliable in their judgments of when the fibers were at their TMs, and indeed, some individuals did seem uncertain in their judgments. Another possibility is that the fibers touched participants' TMs at different locations across sets of measurements. This is highly plausible, because there is no single TM location, as it slants sharply, spanning a length of ~6 mm from the top of the drum to the vertex. Additionally, the probe tubes may have moved while in participants' ear canals. Although participants were asked to remain still and quiet during the measurements, a chin/head rest was not used, and participants were allowed to talk between measurements. Other researchers have also found that small movements by the participants cause appreciable variability in the measured response.

As a final consideration, it is unlikely that the experimenter was able to insert the probe tube, and adjust its depth with a high degree of precision, given the manual nature of the procedure. And, even if the experimenter had been successful with this task, the probe tube angle and transverse location in the ear canal were not controlled. These variables may cause differences of up to 1.3 mm (4 mm average).

Despite these many potential sources of variability, the probe tube position varied by an average of only 0.8 mm (0.54 SD; 2.5 mm maximum) across the three sets of measurements at the different locations in the ear canal (the error was estimated based on the variation in the pressure-minima-derived distance from the TM). Had the experimenter been less concerned with good reproducibility, and had a special probe-tube vent not been used, it would likely have been poorer.

Figure 6:
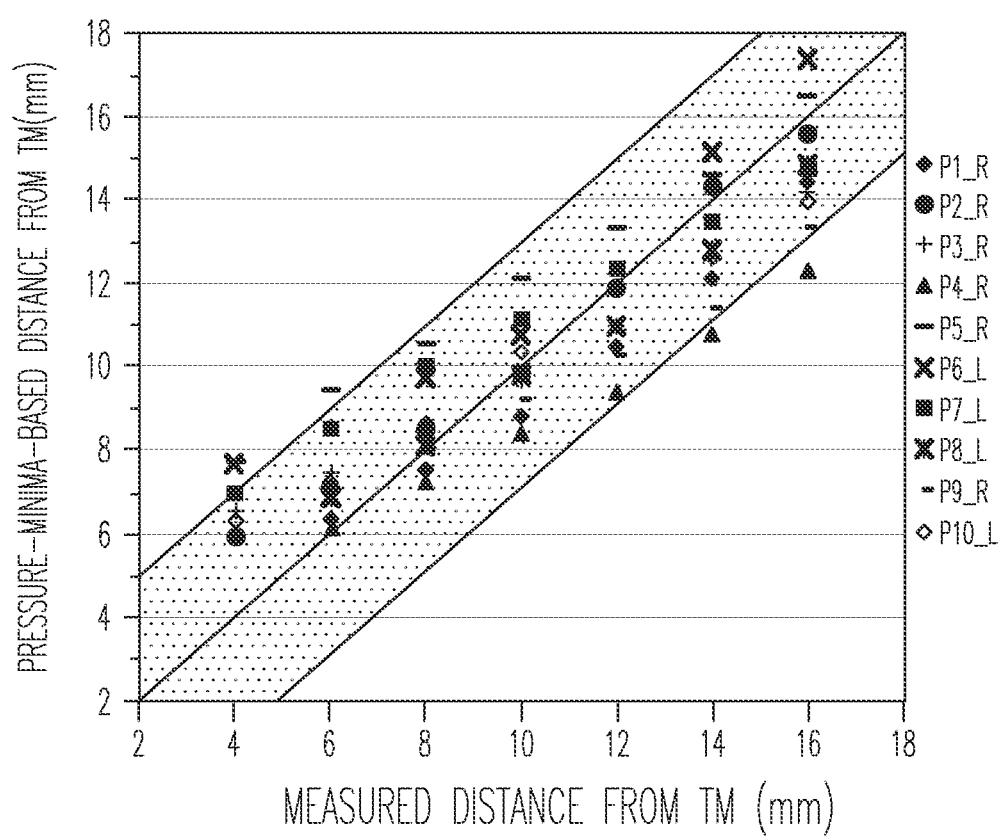
FIG. 6 illustrates comparisons of the measured and estimated distances from the TM according to an embodiment of the present subject matter.

As a final check of probe tube placement, the pressure minima-derived-distances to the TM were compared with the measured distances to the TM. FIG. 6 shows that the two were highly correlated (0.912), with pressure-minima-based distances generally falling within ±3 mm of the measured distance. The data show that very close to the TM, the pressure minima over-estimated the distance to the TM. This may have occurred because the effective reflecting surface of the TM changes from a location toward the top of the TM to one closer to the vertex, as the measurement location moves closer to the TM.

SPL Variations Along the Ear Canal

In an embodiment, the initial measurement for most individuals occurred at a distance of 2 mm from the TM. Therefore, it is of interest how accurately this measurement reflects the SPL at the TM. Measurements made at the TM for two individuals showed that the 2 mm response was within 3 dB of the TM response through 16 kHz for one individual (FIG. 7), and through 12 kHz for the other individual. These results indicate that the 2 mm response provides a reasonable estimate of the SPL at the TM.

Figure 7:
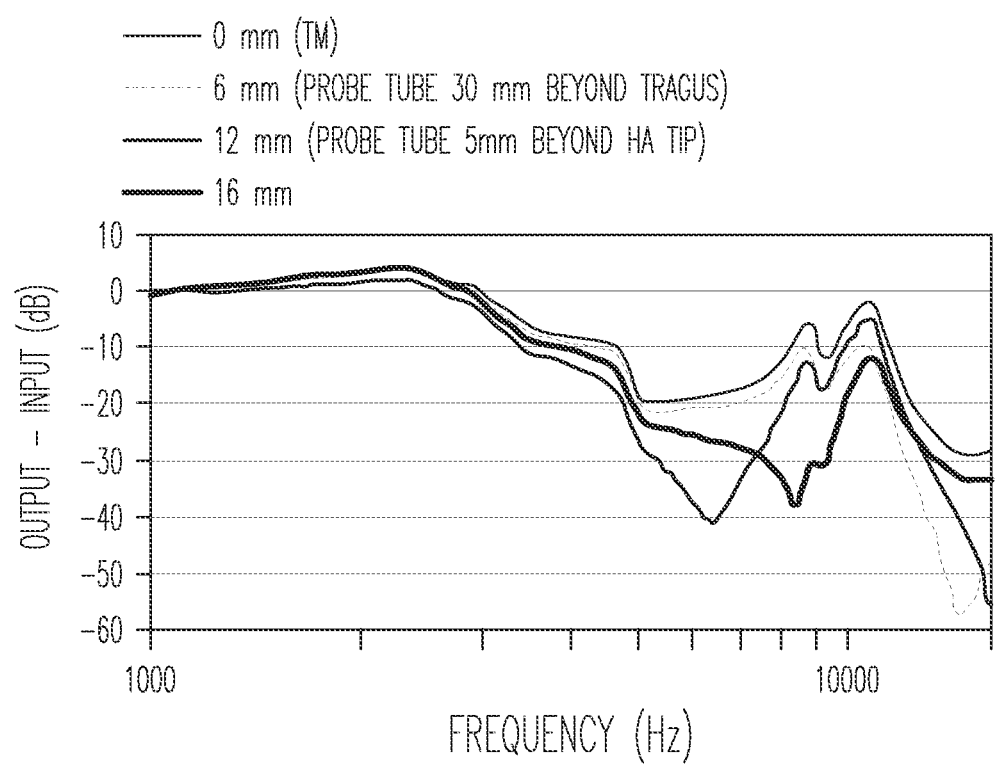
FIG. 7 illustrates measured frequency responses at different locations in the ear canal according to an embodiment of the present subject matter.

Measurements for all participants showed the shift of the pressure minima to lower frequencies the greater the distance from the TM. This reduces the highest frequency at which the measured response accurately represents the SPL at the TM. As an example, FIG. 7 shows that responses were within 3 dB of the TM response through 8150 Hz at 6 mm, 4300 Hz at 12 mm and 2750 Hz at 16 mm. For this individual, 6 mm corresponded to the distance at which real-ear measurements would be performed using the measurement technique of marking the probe tube at 30 mm and placing the mark at the inter-tragal notch. At 12 mm from the TM, the probe tube extended 5 mm beyond the medial tip of the in-ear monitor; this is the minimum distance recommended to avoid transition field effects, which affect the accuracy of high-frequency measurements. At the 16 mm position, the probe tube would have extended only 1 mm beyond the tip of the in-ear monitor. Frequencies below 3 kHz were generally within 5 dB of the TM response, regardless of the probe tube location in the ear canal. As shown, there are trade-off between probe tube depth and measurement accuracy when performing real-ear measurements.

SPL Estimation

Figure 8A:
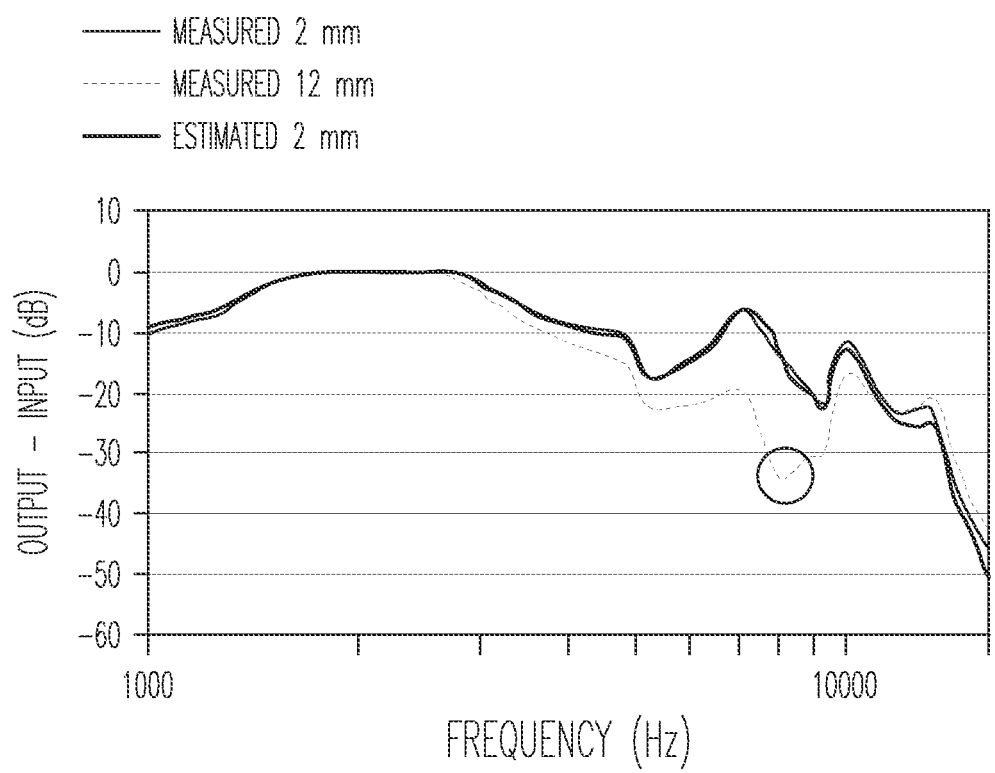
FIGS. 8A-8B illustrate measured and estimated responses and a corrected frequency response chart according to an embodiment of the present subject matter.
Figure 8B:
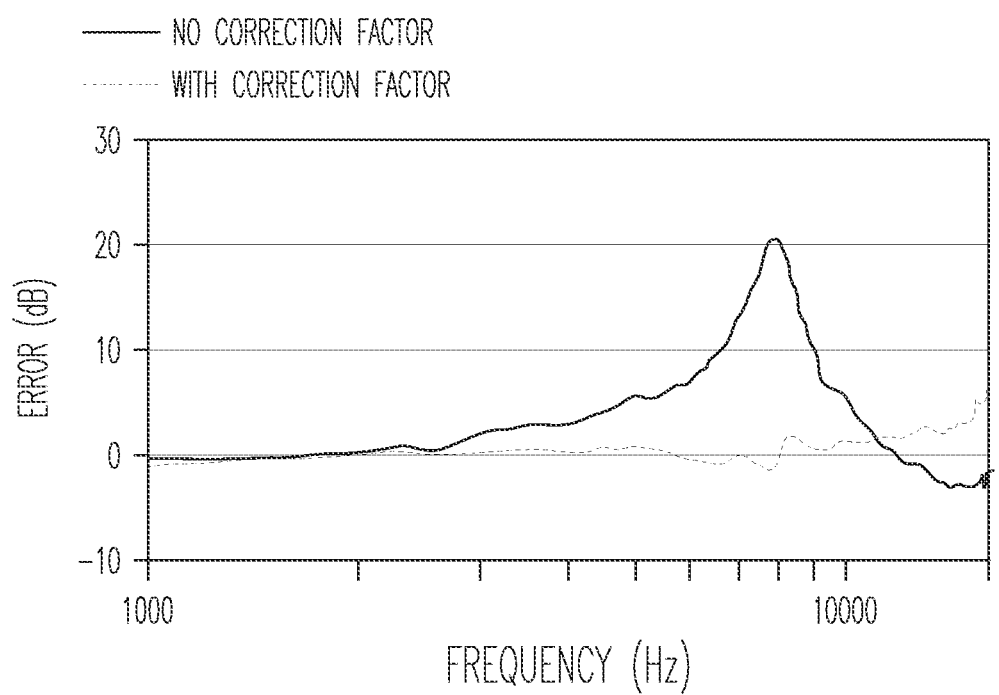

To verify that the correction factors improved the accuracy of the estimated SPL at the TM, the estimated distance to the TM for each measurement along the ear canal was determined, the appropriate correction factor was added, and the estimated response was compared to that individual's measured response at 2 mm from the TM. FIGS. 8A and 8B illustrate, as an example, for participant #8, at a distance of 12 mm from the TM, the dominant pressure minima (e.g., a null frequency) occurred at 7900 Hz. The ¼ λ wavelength of this frequency is ~10.9 mm. Therefore, we added the correction factor for a pressure-minima-based distance of 11 mm (FIG. 2) to this response (e.g., the output). The new (estimated) frequency response was compared to the measured response at 2 mm from the TM. In this example, the estimated SPL and the measured SPL showed a good match. Without the correction factor, the response 12 mm from the TM was within 3 dB of the 2 mm response only through 4000 Hz; with the correction factor, the two responses were within 3 dB of each other through 14,550 Hz.

Figure 9A:
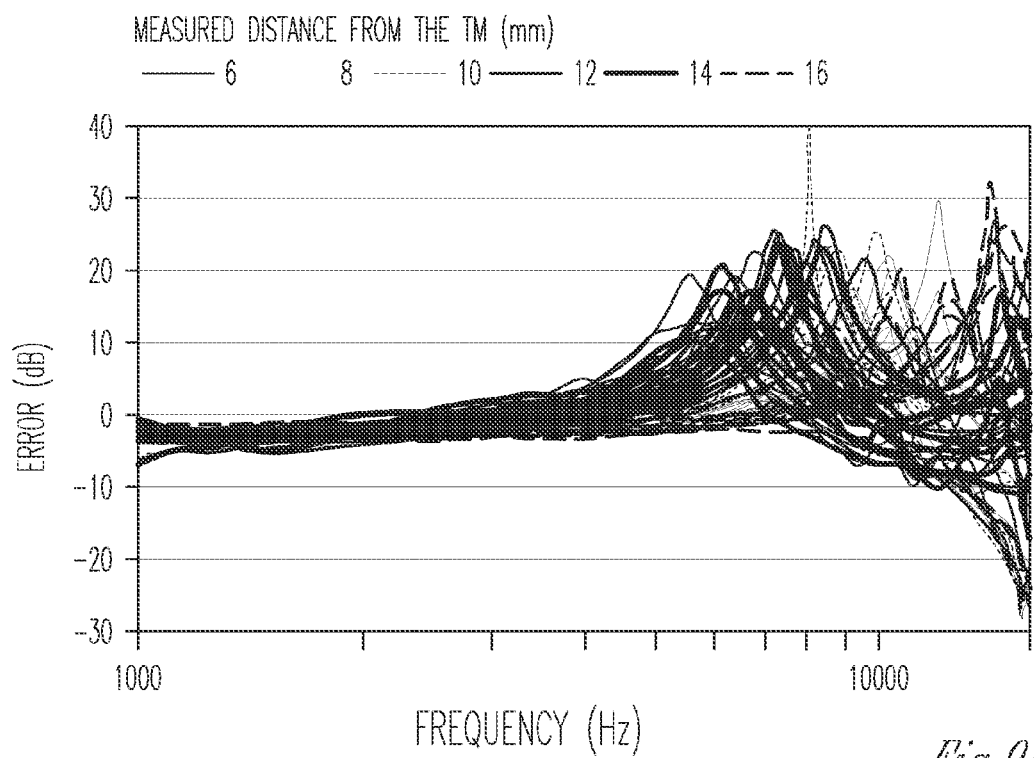
FIGS. 9A-9B illustrate measurement error without the correction factors (9A) and with the correction factors (9B) according to an embodiment of the present subject matter.
Figure 9B:
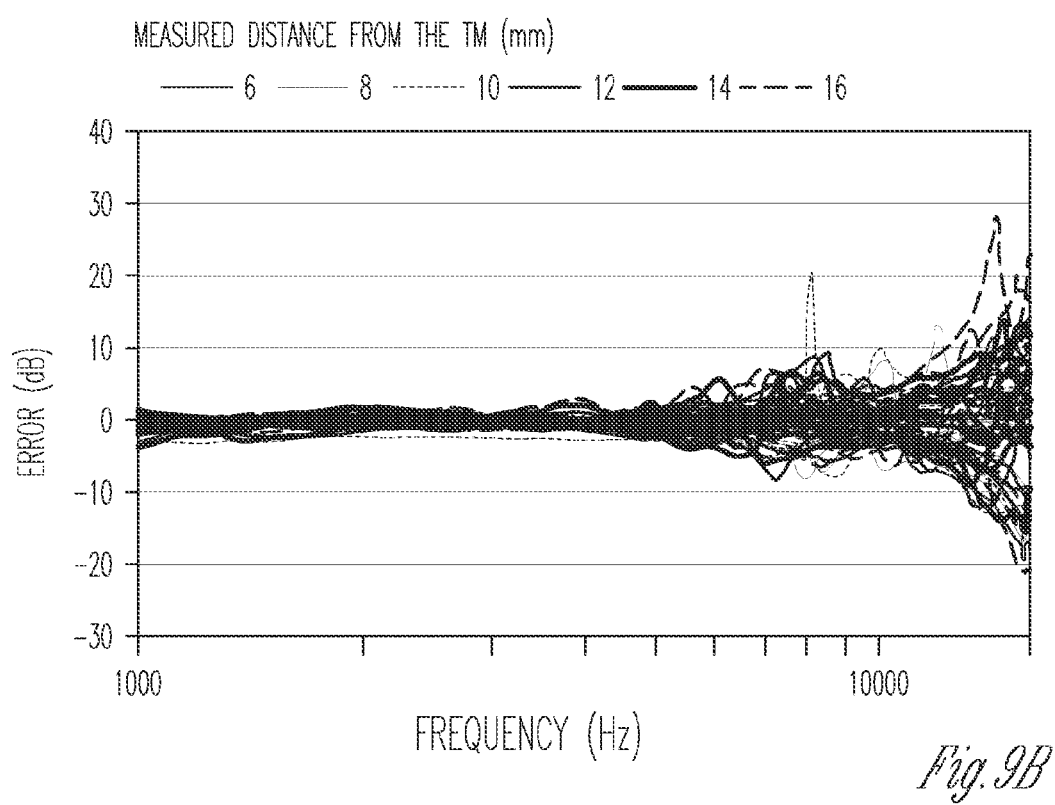
Figure 10A:
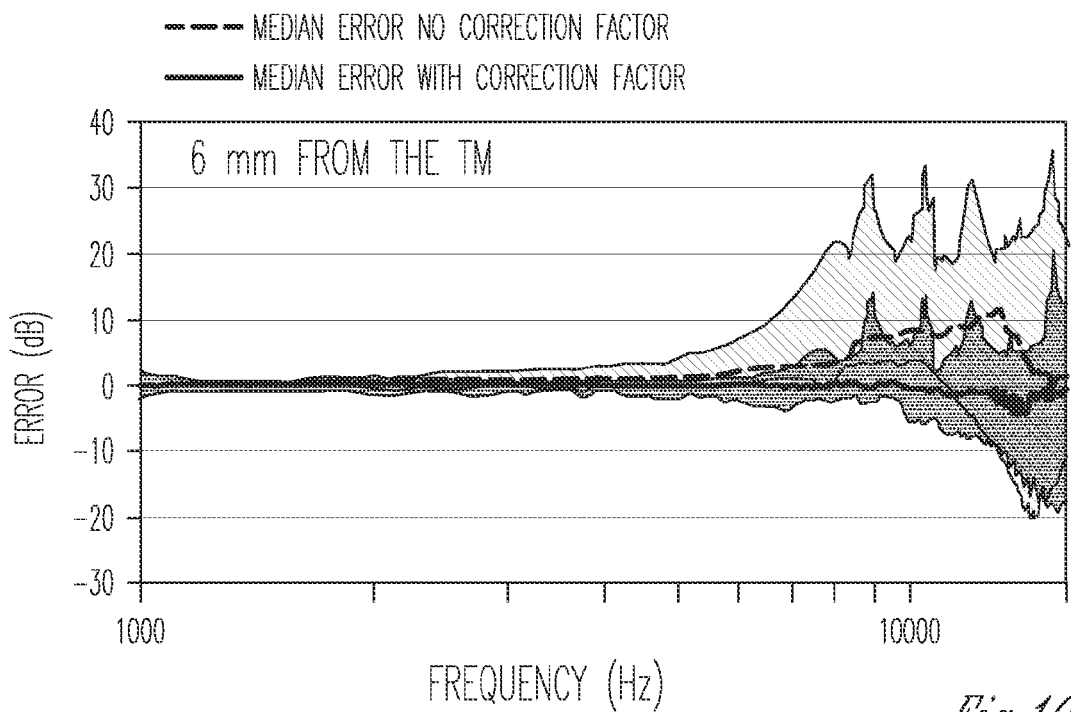
FIGS. 10A-10F illustrate measurement error with and without the correction factors for each of the measured distances along the ear canal according to an embodiment of the present subject matter.
Figure 10B:
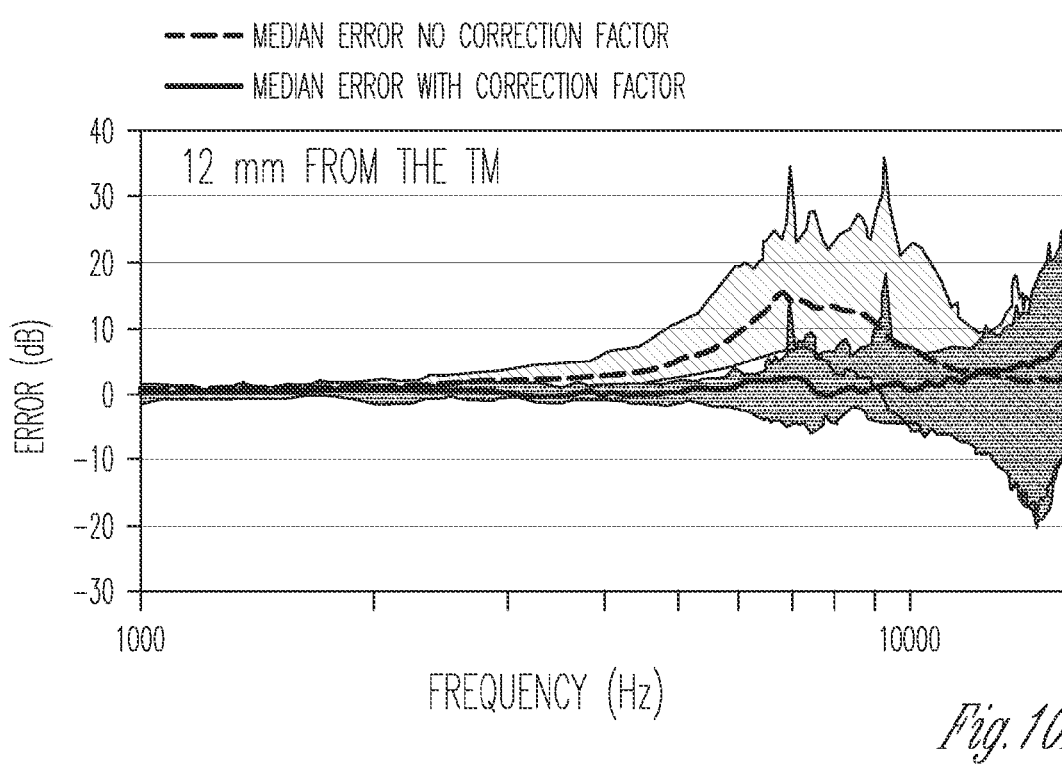
Figure 10C:
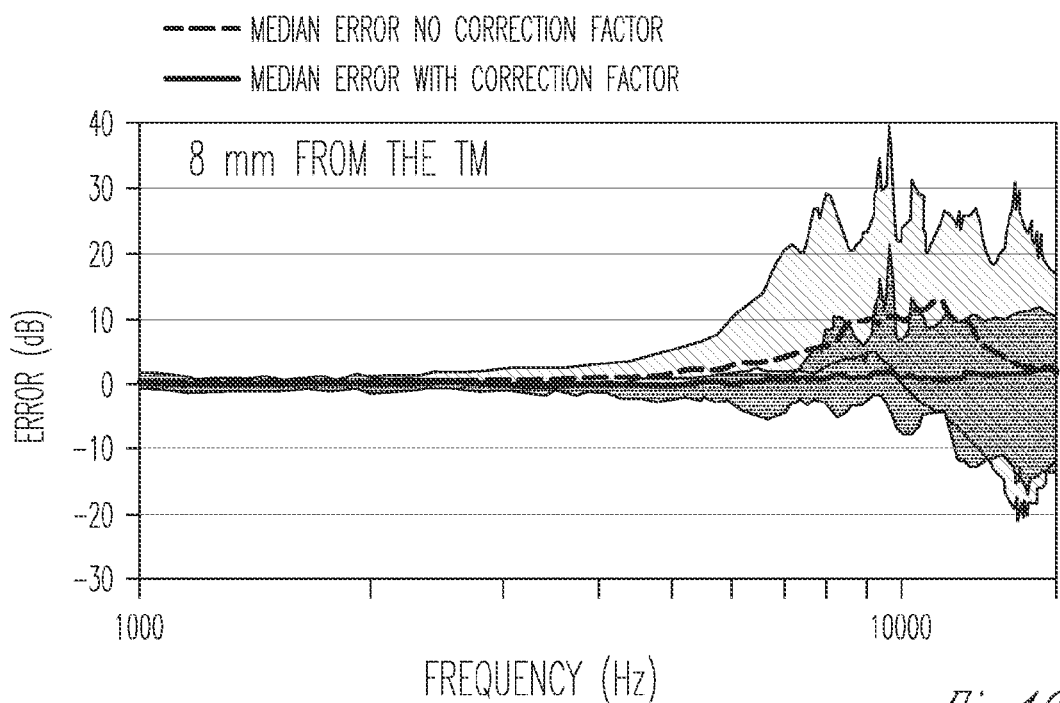
Figure 10D:
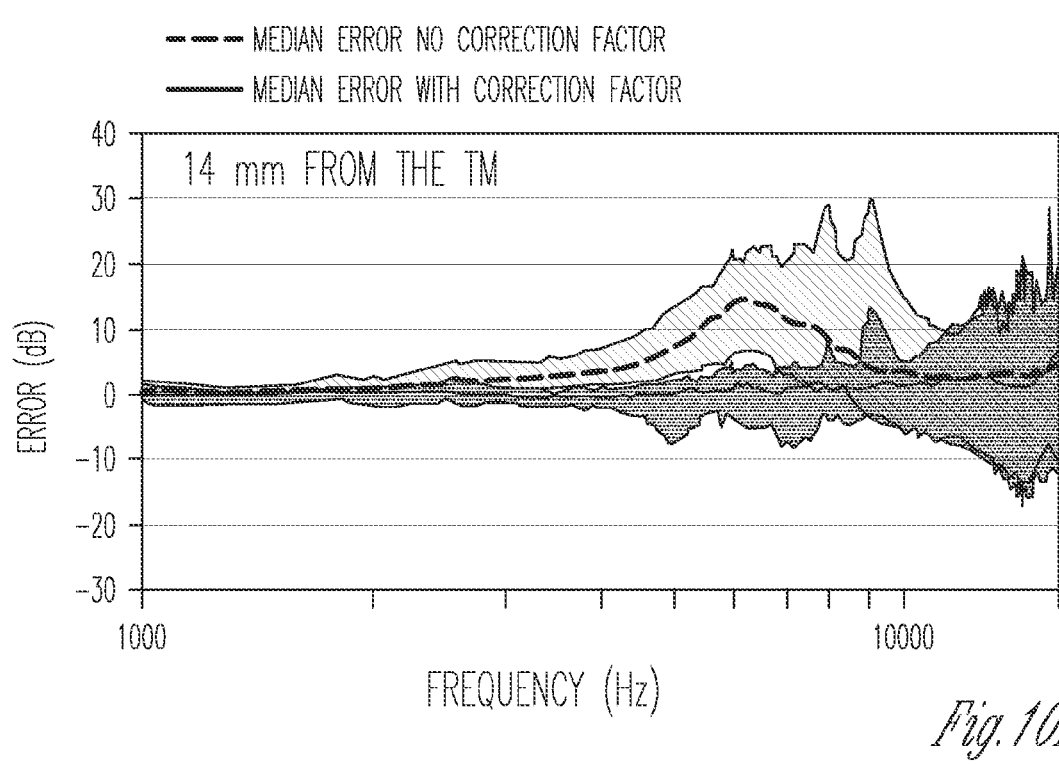
Figure 10E:
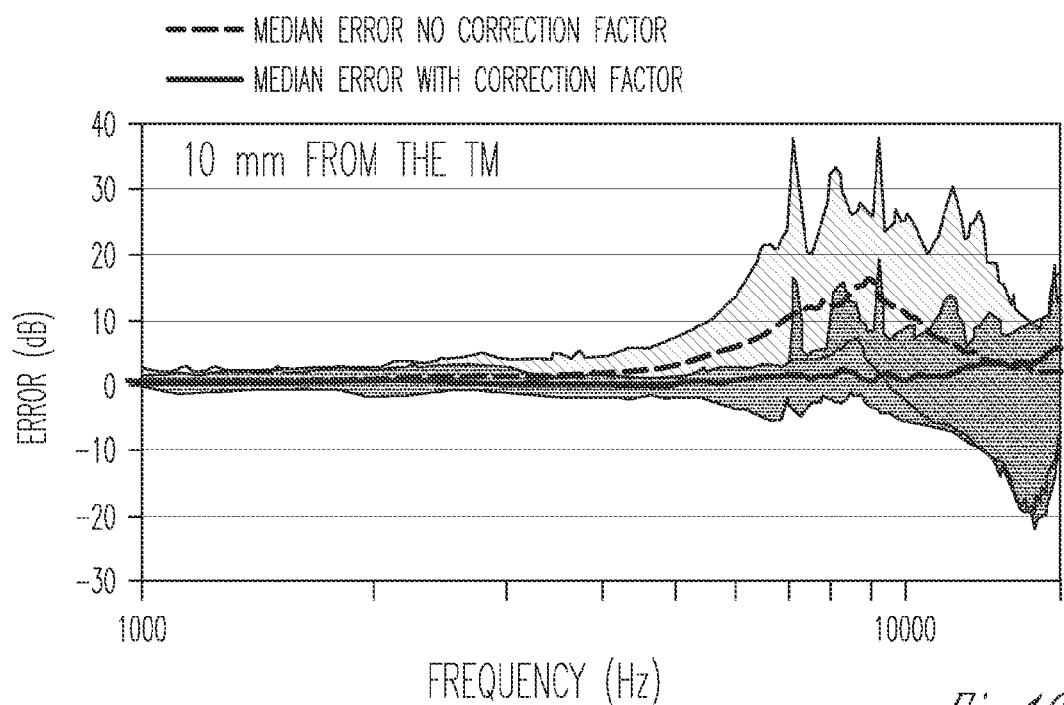
Figure 10F:
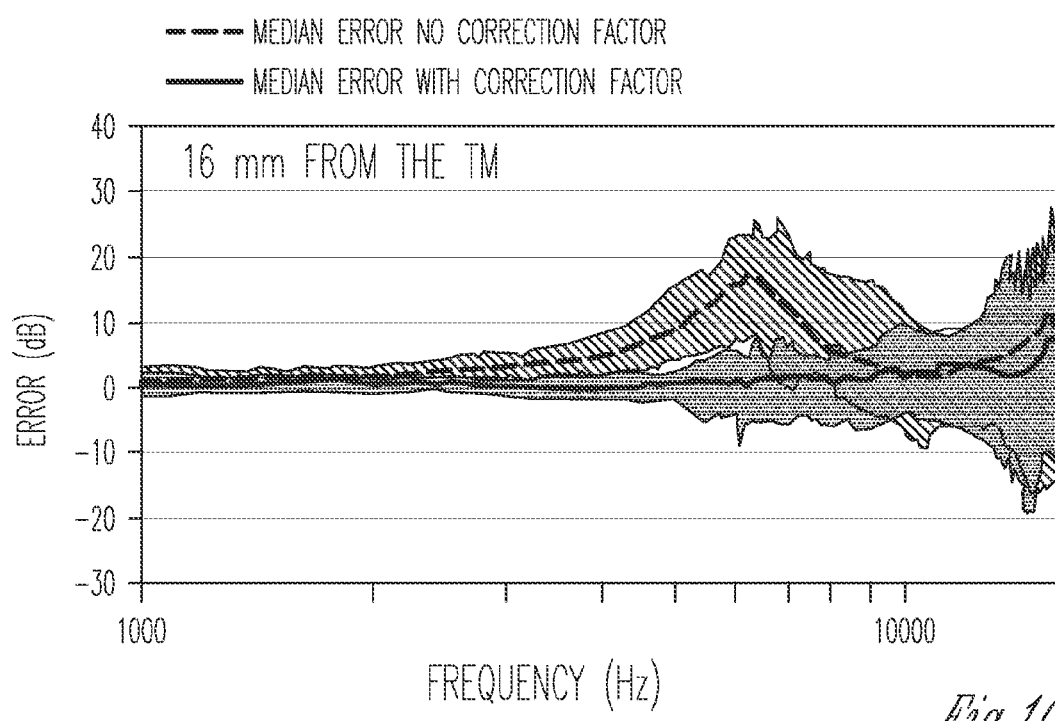
Figure 11A:
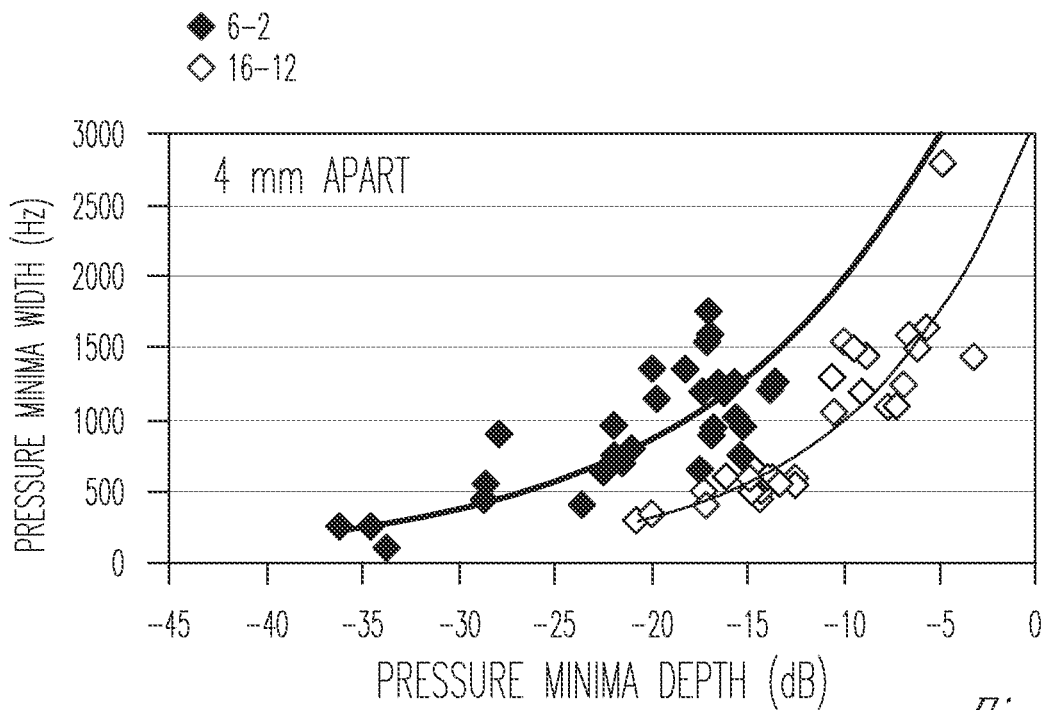
FIGS. 11A-11F illustrate a correlation between the pressure minima depth and pressure minima width (3 dB from maximum), for various measurement locations in the ear canal according to an embodiment of the present subject matter.
Figure 11B:
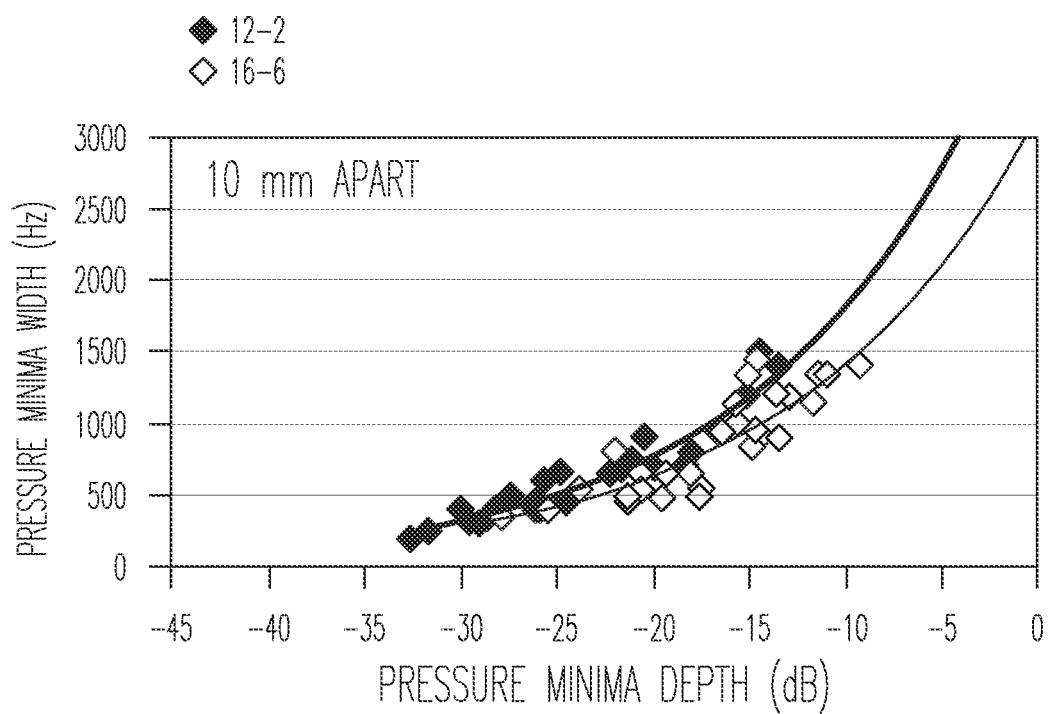
Figure 11C:
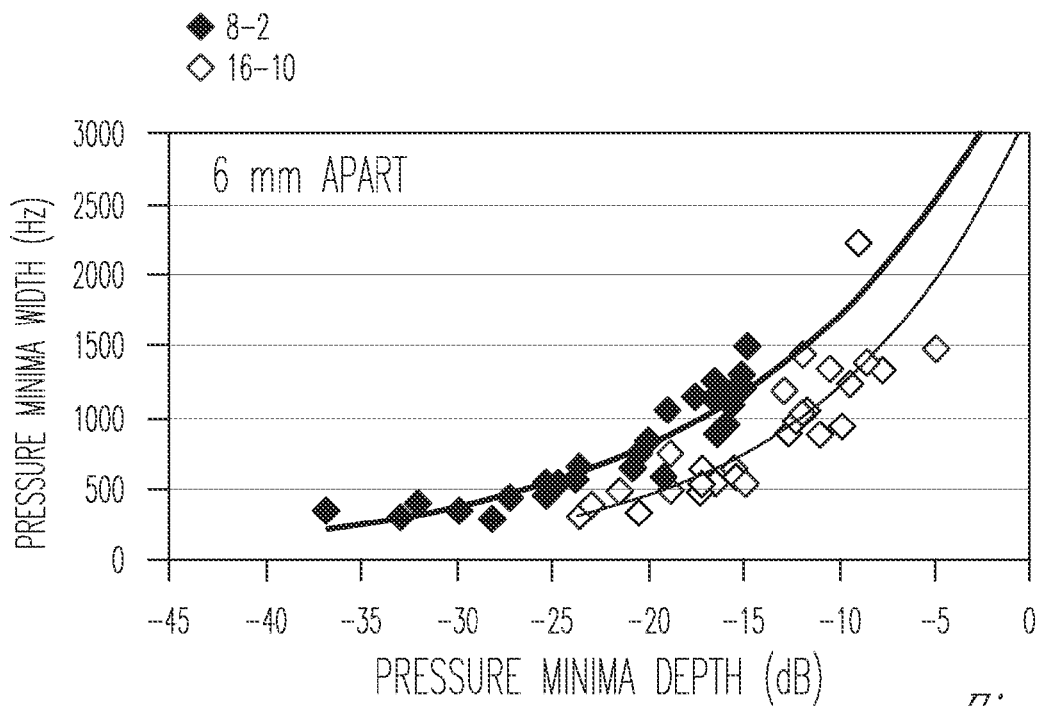
Figure 11D:
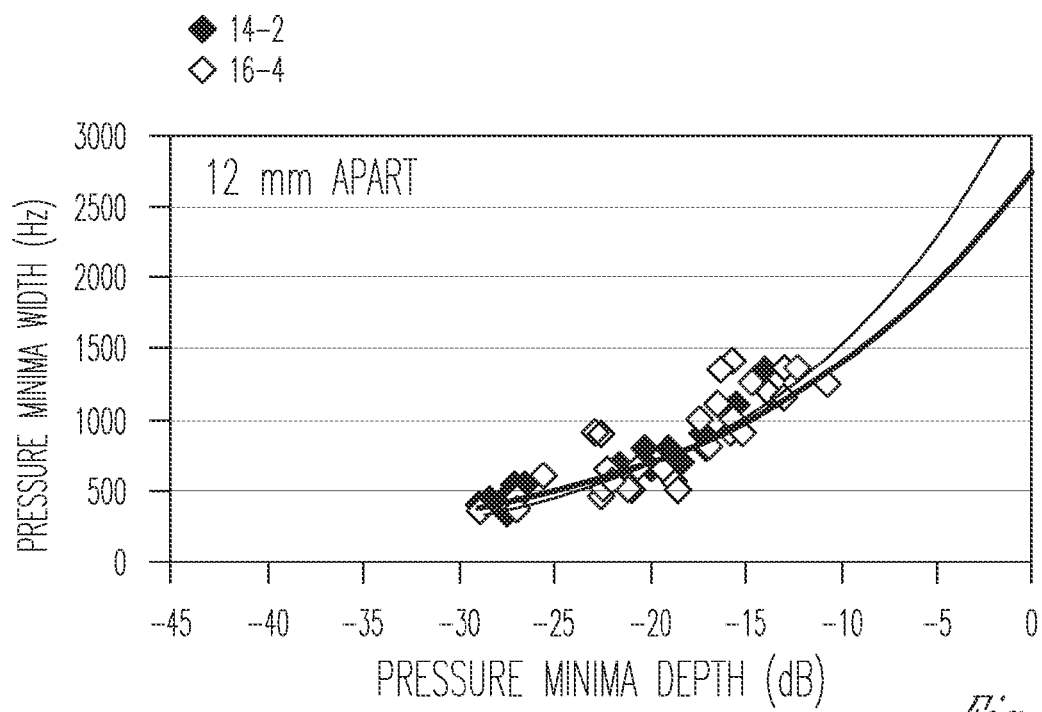
Figure 11E:
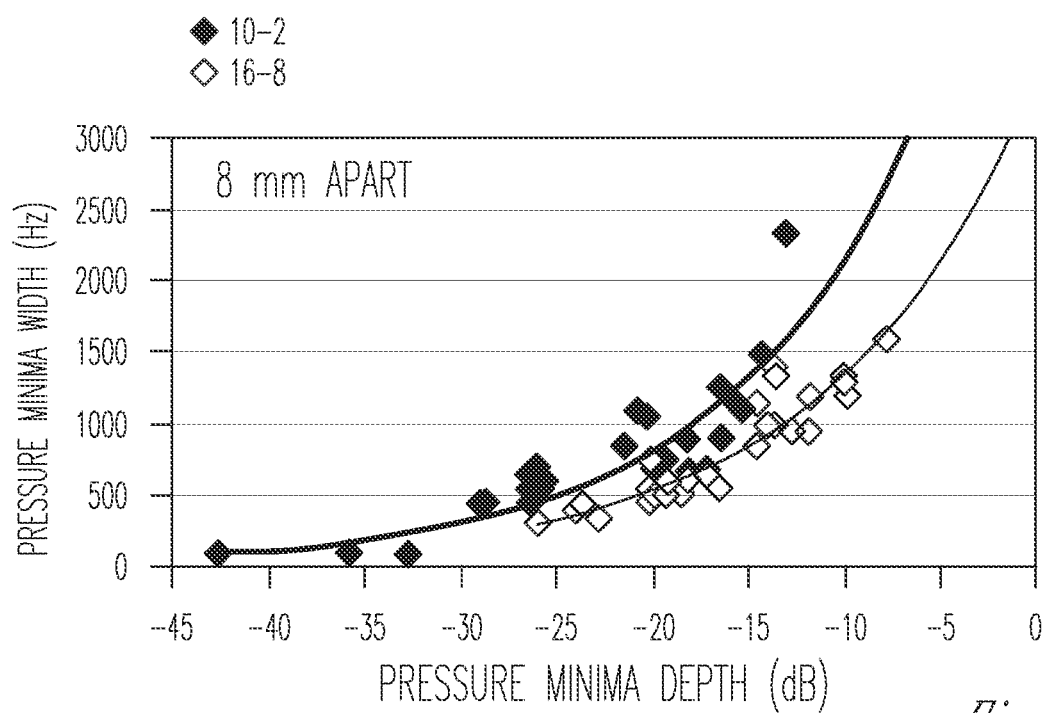
Figure 11F:
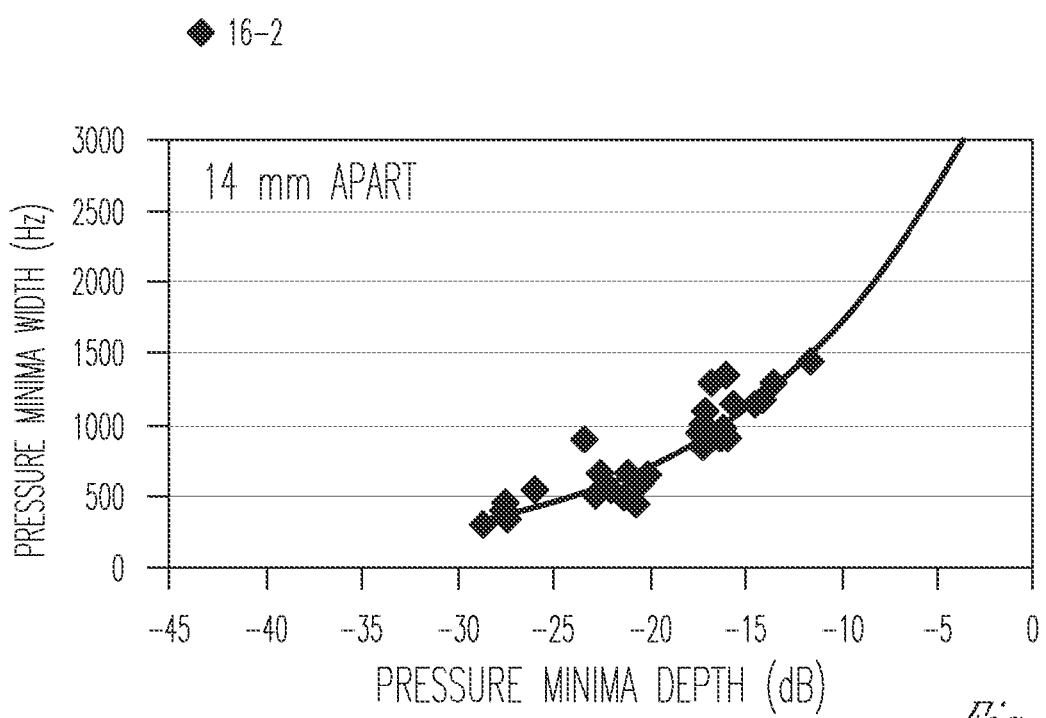

FIGS. 9A and 9B illustrate graphs that plot the amount of error for a group of individuals. In this figure, there is one curve plotted for each participant at each of the measured distances from the TM. There are several noteworthy points regarding this figure. First, the maximum error shifts lower in frequency with increased distance from the TM. Second, at a given distance from the TM, there is a large amount of variability across individuals in the frequency, depth and width of the pressure minima. Lastly, the amount of error is large, on the order of 20-30 dB or higher, even for frequencies as low as 5000 Hz. Once the correction factors were added to the measurements, the amount of error was reduced considerably. With two exceptions (both at 10 mm from the TM), the estimated responses were within 10 dB of the 2 mm response through 11 kHz.

In an embodiment, the correction factors were used on a new group of measurements performed on different ears. Measurements were made on a second group of 10 individuals, the "verification" group. FIGS. 10A-10F show, for each measured distance from the TM, the range of error for the group when the correction factors were not used (light shaded region), when they were used (dark shaded region), and the median error for both conditions.

FIG. 15 shows a summary of the absolute error at each 1000 Hz interval, with and without the correction factors. Differences of ≥3 dB are shaded. Improvements ≥3 dB were seen through 15 kHz at 6 mm from the TM, 12 kHz at 10 mm from the TM and 9 kHz at 14 mm from the TM. At the frequency of the dominant pressure minima, the error typically decreased by 16-22 dB ($10^{th}/90^{th}$ percentiles); although in some cases the remaining error was still quite large, in some cases greater than 20 dB.

In an embodiment, the correction factors do not increase the amount of error over not using correction factors. In an embodiment, for the verification group, the error never increased for any measurement by more than 3 dB through 9 kHz (within 12 mm of the TM), or 6 dB through 11 kHz (at all locations along the ear canal). And, only at a single frequency was the average error greater by ≥3 dB by applying a correction factor (16 kHz, at 10-14 mm from the TM).

Figure 16:
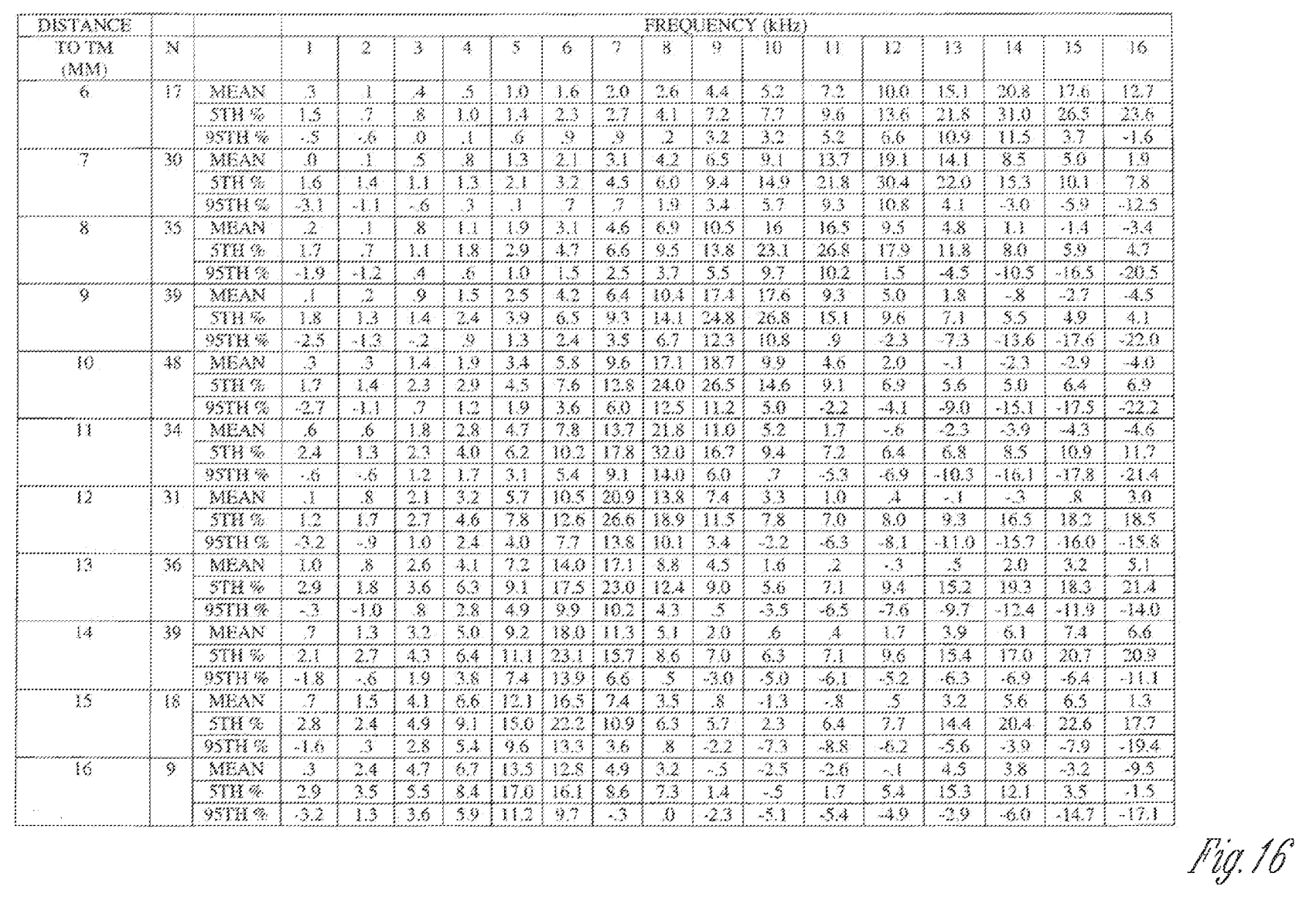

In an embodiment, the data from all 20 participants was collapsed to create new correction factors. The mean, $5^{th}$ and $95^{th}$ percentiles for each of the estimated distances from the TM are provided in 1000 Hz intervals in FIG. 16. Collapsing the data for the two groups did not change the original correction factors by more than 2 dB for any 1000 Hz interval ≤12 kHz or by more than 4 dB through 16 kHz.

Discussion

For extended bandwidth hearing aids to become a clinical reality, audiologists and hearing aid dispensers will require a safe, fast, and accurate method to verify the high-frequency SPL at the TM. In this article, we have described a technique that improves the estimated SPLs at the TM, through 9-15 kHz, depending on the measurement location. Additionally, this technique provides several advantages over other available options, including:

(1) Minimal information is required. One need not know the specific geometry or acoustic properties of an individual's ear canal or middle ear, nor does one need to know the exact measurement distance from the TM. For most individuals, a single measurement in the ear canal, away from the TM, will allow the identification of the frequency of the dominant pressure minima, which will determine which correction factor to apply.

(2) Because this technique follows typical real-ear measurement procedures, there is no greater risk, and it is no more invasive, than real-ear measurements that are currently performed clinically. Additionally, because these measurements are of sound pressure, rather than sound intensity, they are in a unit that is already familiar to practicing audiologists and hearing aid dispensers.

(3) By design, this technique decreases the amount of error where it is needed the most, in some embodiments by 16-22 dB at the frequency of the dominant pressure minima. At the same time, using the correction factors rarely increased the amount of error over not using the correction factors.

(4) If a real-ear measurement system automated the steps of identifying the pressure minima and adding the correction factors to the measured responses, the measurement time should not increase.

Figure 13A:
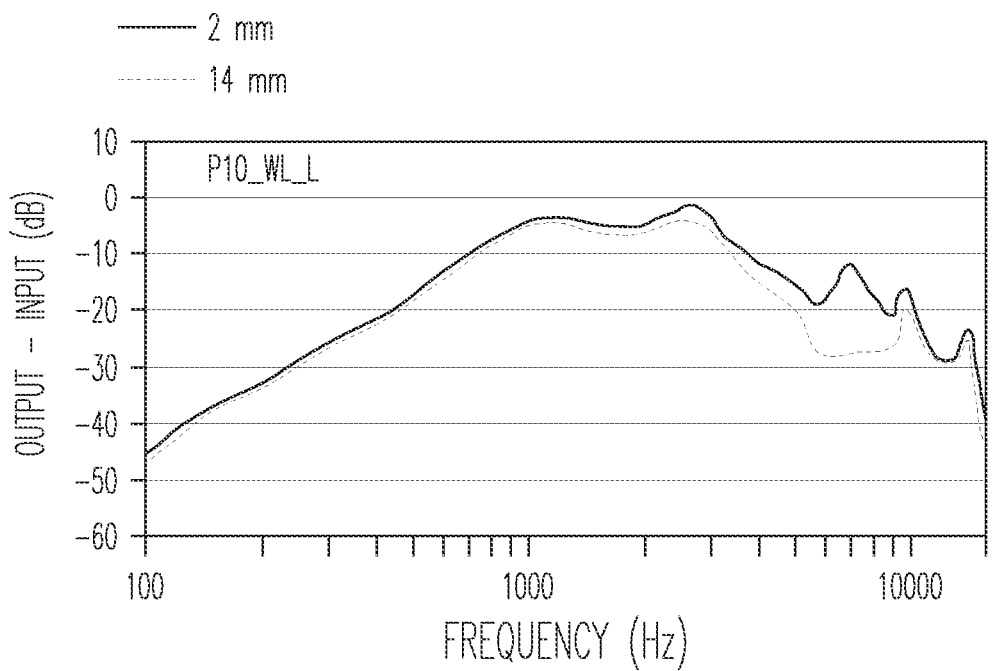
FIGS. 13A-B illustrate graphs depicting measurements from 14 mm and normalized to 2 mm according to an embodiment of the present subject matter.
Figure 13B:
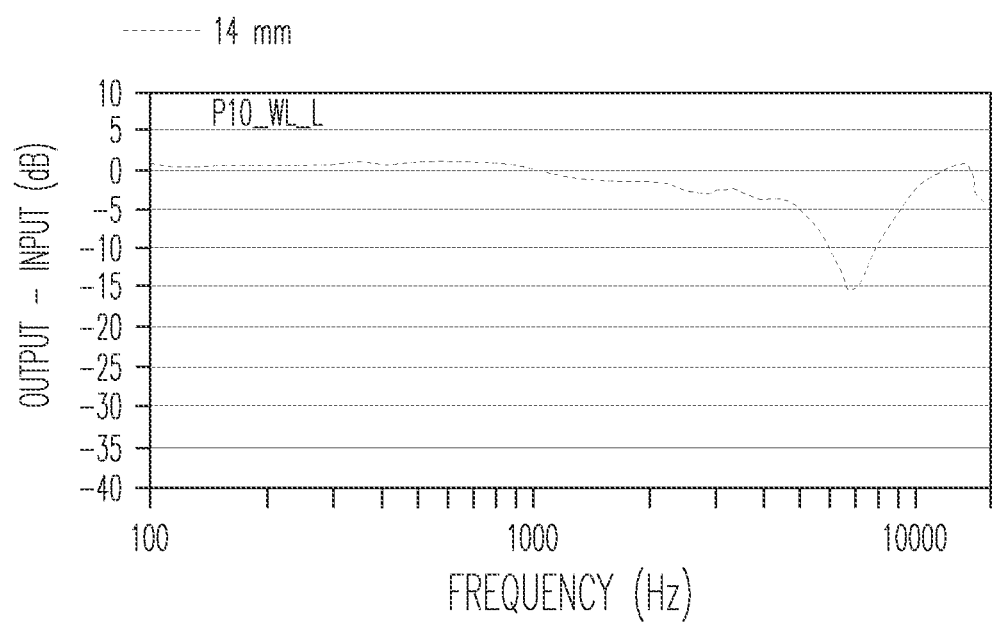

In some embodiments, the method is modified. For example, while the frequency of the dominant pressure minima can often be identified by a single measurement in the ear canal, this is not always the case, as naturally-occurring dips in the frequency response can obscure the pressure minima; an example of this can be seen in FIG. 13A, with the measurement that is 14 mm from the TM. When this occurs, the probe tube can be moved to another location in the ear canal, and another measurement can be made. If the pressure minima are not readily identifiable in this measurement, the two measured responses can be normalized to each another to determine the frequency of the dominant pressure minima, as in FIG. 13B. Based on our measurements for the reference group, the estimated distance to the TM varied by an average of less than 0.5 mm (1.78 mm maximum) regardless of which two points along the ear canal were used to make the estimate, with the estimated distance increasing the farther the two measurements were from the TM.

Because the depths and the widths of the pressure minima were highly variable, even among adults with normal middle and external ear properties, applying a correction factor may not get every measurement within a certain dB criteria of accuracy, and the amount of remaining error for some measurements was substantial, in some cases >20 dB, especially at the highest frequencies tested. For a given measurement, the estimated response was off to the extent that that individual's transfer function differed from average. Therefore, it is of interest whether the correction factors could be customized to the individual based on certain patient information or by gleaning additional information from the measurements themselves. As a preliminary step toward answering this question, we performed the Pearson Product Moment Correlation statistic to determine whether there was a significant correlation between the depths or the widths of the pressure minima and the participants' ear canal lengths, ear canal volumes or TM compliances. (Ear canal length was estimated as the distance between participants' inter-tragal notches and TMs, as measured by inserting probe tubes into participants' open ear canals and having them report when the fibers were at their TMs; ear canal volume and TM compliance were both estimated from participants' tympanometric results.) Results showed that the depths of the pressure minima were uncorrelated with these variables, and the widths of the pressure minima showed only a slight correlation (0.196) with ear canal length (p=0.032). However, the sample size in this study was small, and our measurement techniques for these parameters were crude, and so it is possible that larger sample sizes and more accurate measurement techniques would find stronger correlations among these variables. Furthermore, because ears, and their related structures, differ in size and impedance across different populations, the correction factors presented in this article should be verified on populations known to have different ear characteristics, especially children and those with conductive hearing losses.

Figure 14:
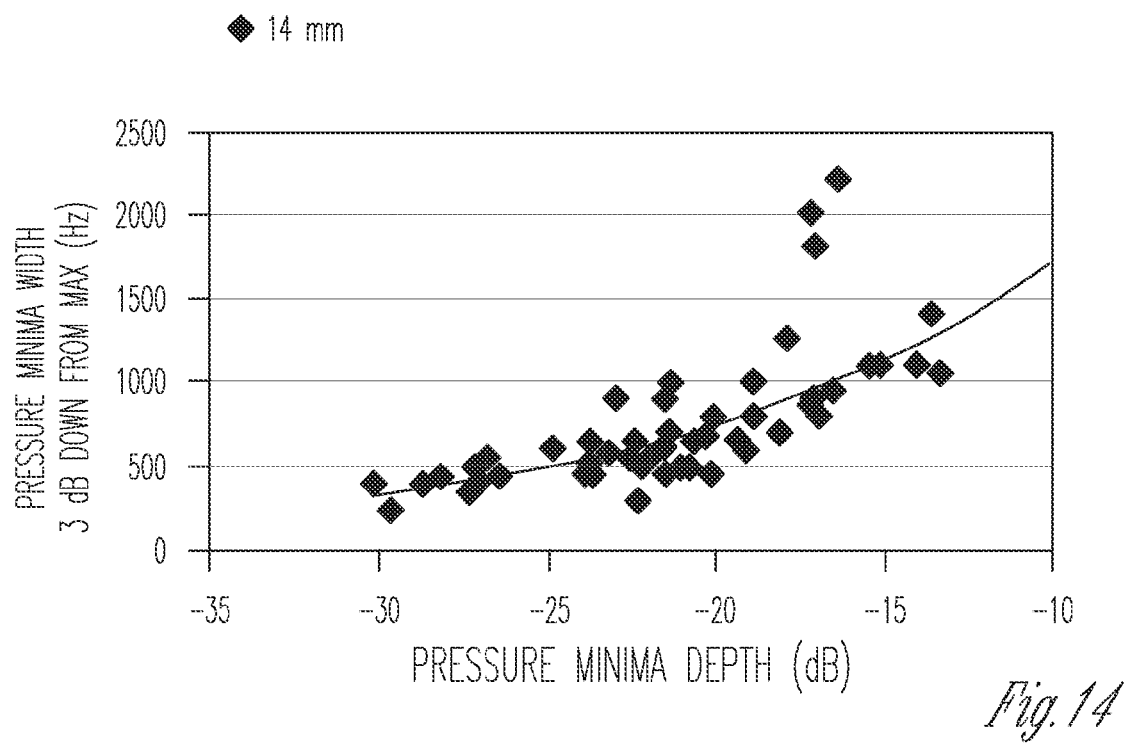
FIG. 14 illustrates the relationship between pressure minima depth and pressure minima width according to an embodiment of the present subject matter.

That said, a few interesting trends emerged from the data that suggest that customization of the correction factors may be possible, especially if two measurements are made at different locations along the ear canal. First, as previously mentioned, the estimated distance to the TM was fairly stable regardless of which two points along the ear canal were used to estimate it. Second, the widths of the pressure minima (3 dB from maximum) were also fairly stable. Excluding one outlier, the pressure minima widths varied by an average of <200 Hz (450 Hz max), as long as the two measurements were at least 4 mm apart in the ear canal; at closer distances, the widths tended to increase. Lastly, there was a strong correlation between the depths of the pressure minima and the widths of the pressure minima, between 0.758 and 0.926, depending on the distance between the two measurements and their locations in the ear canal (FIGS. 11A-11F). (To simplify this figure, only the extreme examples were plotted—where the measurements were closest to and farthest from the TM, for measurement locations 4, 6, 8, 10, 12 and 14 mm apart. For example, the top left plot shows two sets of data—when the 6 mm response was normalized to the 2 mm response, and when the 16 mm response was normalized to the 12 mm response, both examples of measurements that were 4 mm apart). Collectively, these results suggest that almost any two points along the ear canal, ≥4 mm apart, can provide a reasonable estimate of the frequency, width and depth of the pressure minima. As an example, normalizing the 14 mm response in FIG. 13A to any other measurement along the ear canal gave an estimated distance to the TM of approximately 13 mm (12.6-13.4 mm) with a 1100-1500 Hz pressure minima width, and using the trend line in scatter plot of FIG. 14, gave an estimated pressure minima depth of approximately −12 to −16 dB (the actual depth was −15.4 dB). Optimizing the use of this information will be the focus of future investigations.

Figure 12:
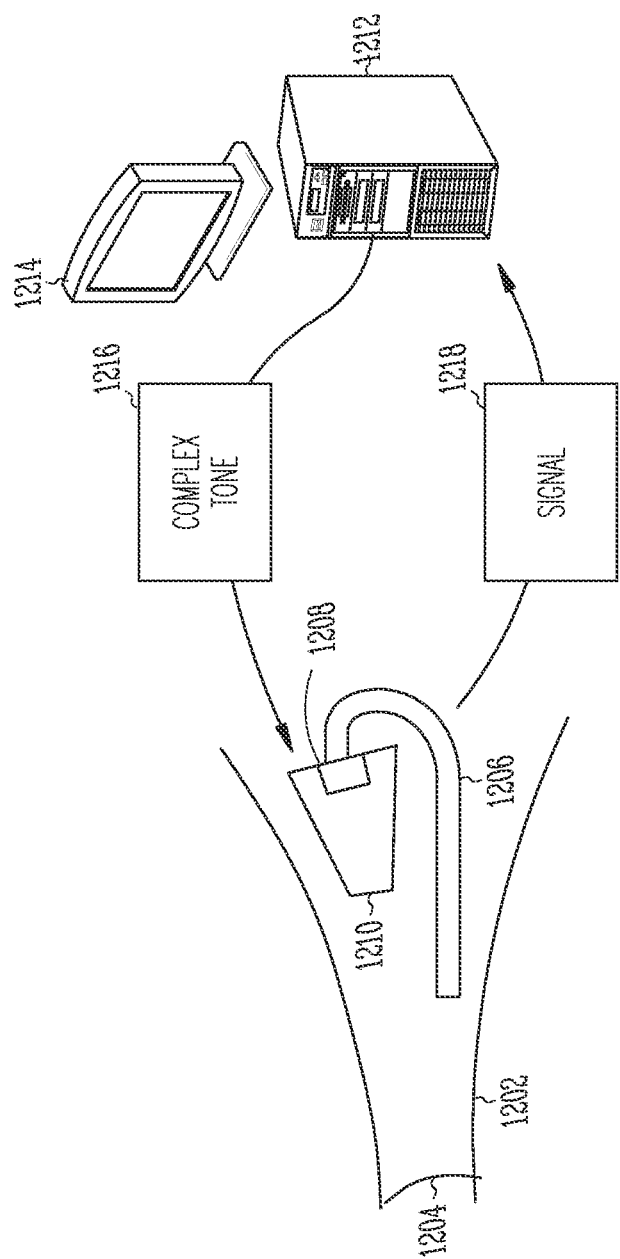
FIG. 12 illustrates a system of estimating the SPL at the TM according to an embodiment of the present subject matter.

FIG. 12 illustrates an example system according to the present subject matter. Illustrated is ear canal 1202 with tympanic membrane 1204. Hearing aid 1210 includes microphone 1208 with probe 1206 attached to microphone 1208. Further illustrated is computing device 1212 with one or more processors capable of executing instructions (e.g., personal computer, server, personal digital assistant, mobile electronic device) and display device 1214. In an embodiment, complex tone 1216 is sent to hearing aid 1210. This may be done wireless over protocols such as Wi-Fi (802.11a/b/g/n), Bluetooth, RFID or with a direct wireless or pin connection. Complex tone 1216 is played by hearing aid 1210 into ear canal 1202. The resulting signal 1218 is picked up or recorded by microphone 1208 and sent to computing device 1212 where a frequency analysis is performed.

In various embodiments, the frequency analysis produced output as a function of the frequency. The output is further analyzed to determine a null frequency (e.g., dominant pressure minima). Finding the ¼ wavelength of the null frequency results in the estimated distance from the microphone to the tympanic membrane. Based on predetermined correction factors associated with various distances (e.g., FIG. 16), the output can be corrected to estimate the sound pressure level at the tympanic membrane as a function of frequency. The output may be presented on display device 1214. In various embodiments this process may be repeated a second time using the same or different complex tone as well as at the same or a different distance.

Figure 17:
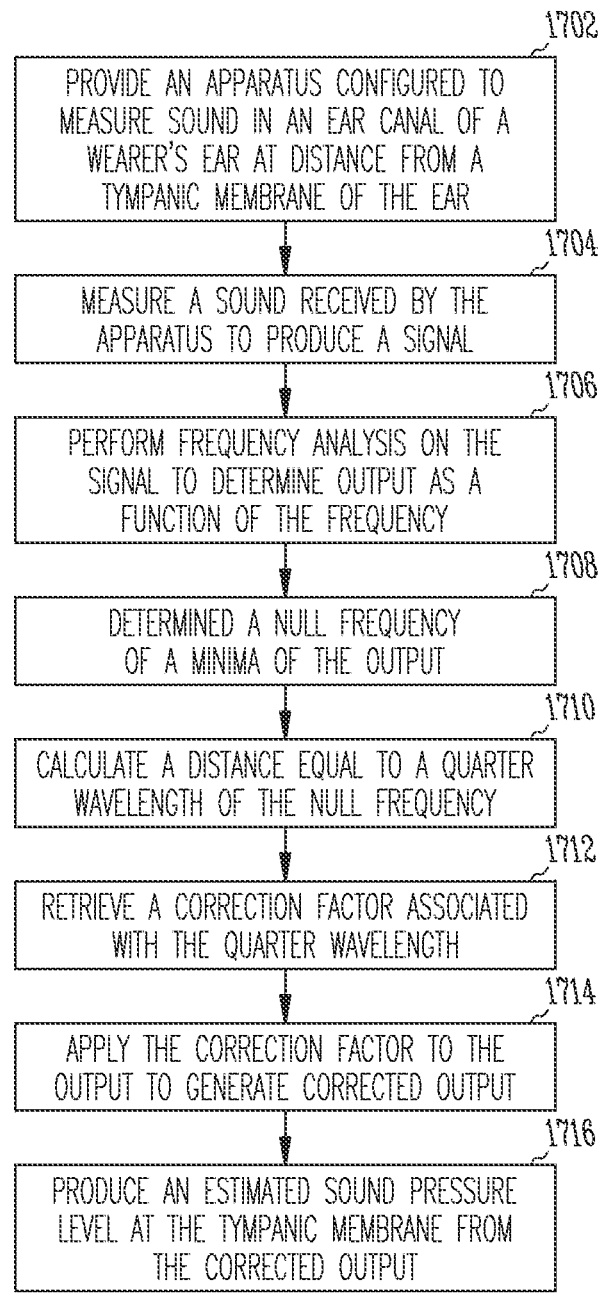
FIG. 17 is a flow chart of a method of producing estimated SPL levels at the TM according to an embodiment of the present subject matter.

FIG. 17 illustrates an example method of the present subject matter. At block 1702 an apparatus is provided configured to measure sound in an ear canal of a wearer's ear at a distance from a tympanic membrane of the ear. At block 1704, the sound is measured received by the apparatus to produce a signal (e.g., a response). At block 1706, a frequency analysis is performed on the signal to determine output as a function of the frequency. At 1708 a null frequency of a minima of the output is determined. At 1710, a distance equal to a quarter wavelength of the null frequency is calculated. At block 1712, a correction factor associated with the quarter wavelength is retrieved. At 1714, the correction factor is applied to the output to generate a corrected output. At block 1716, an estimated sound pressure level at the tympanic membrane from the corrected output is produced.

A method and apparatus has been described to improve the estimated SPL at the TM that requires only the identification of the frequency of the dominant pressure minima, which can often be determined by performing a single SPL measurement in the ear canal, away from the TM. Applying these correction factors resulted in significant improvements in the estimated SPL near the TM, with greater improvements occurring at distances closer to the TM.

What is claimed is:

1. A method, comprising:
   providing an apparatus configured to measure sound in an ear canal of a wearer's ear at a distance from a tympanic membrane of the ear;
   measuring sound at a single location in the ear received by the apparatus to produce a signal;
   performing frequency analysis on the signal to determine output as a function of the frequency;
   determining a null frequency of a minima of the output according to the measurement at the single location;
   calculating a distance equal to a quarter wavelength of the null frequency;
   retrieving a previously generated correction factor associated with the quarter wavelength;
   applying the correction factor to the output to generate a corrected output; and
   producing an estimated sound pressure level at the tympanic membrane from the corrected output.

2. The method of claim 1, wherein performing the frequency analysis includes performing a fast Fourier transform (FFT) on the signal.

3. The method of claim 1, wherein the correction factor is a function of width of the minima.

4. The method of claim 1, wherein the correction factor is a function of depth of the minima.

5. The method of claim 1, further comprising generating a complex tone for sound measurement by the apparatus.

6. The method of claim 5, wherein generating a complex tone for sound measurement includes:
generating a complex test tone with frequencies separated by 50 Hz.

7. The method of claim 5, wherein generating a complex test tone for sound measurement includes:
generating a complex test tone with frequencies at or above 100 Hz and at or below 16000 Hz.

8. The method of claim 1, further comprising generating a swept tone for sound measurement by the apparatus.

9. The method of claim 1, further comprising:
outputting the estimated sound pressure level at the tympanic membrane from the corrected output on a display device.

10. An apparatus for measuring sound pressure level of sound in an ear canal at a tympanic membrane, comprising:
an audio output device to play the sound;
a microphone configured to receive the sound in the ear canal at a first distance from the tympanic membrane and to provide a signal based on the received sound; and
a processor executing instructions configured to:
perform frequency analysis on the signal and determine output as a function of frequency;
determine a null frequency of a minima of the output according to a single measurement at the first distance;
calculate a second distance equal to a quarter wavelength of a wave at the null frequency;
retrieve a previously generated correction factor associated with the second distance, and
apply the correction factor to the output to generate a corrected output related to an estimated sound pressure level at the tympanic membrane.

11. The apparatus of claim 10, wherein the processor is programmed to perform an FFT on the signal.

12. The apparatus of claim 10, wherein the correction factor is a function of width of the minima.

13. The apparatus of claim 10, wherein the correction factor is a function of depth of the minima.

14. The apparatus of claim 10, wherein the sound is a complex tone.

15. The apparatus of claim 14, wherein the complex is a complex tone with frequencies at or above 100 Hz and at or below 16000 Hz.

16. The apparatus of claim 14, wherein the complex is a complex tone with frequencies separated by 50 Hz.

17. The apparatus of claim 10, wherein the sound is a swept tone.

18. The apparatus of claim 10, further comprising a display device to present the estimated sound pressure level at the tympanic membrane from the corrected output.

19. The apparatus of claim 10, further comprising a probe, wherein the probe is attached to the audio output device.

20. The apparatus of claim 10, wherein the processor is configured to send the sound wirelessly to the audio output device.

* * * * *

UNITED STATES PATENT AND TRADEMARK OFFICE
CERTIFICATE OF CORRECTION

PATENT NO. : 8,571,224 B2
APPLICATION NO. : 12/537908
DATED : October 29, 2013
INVENTOR(S) : Recker et al.

It is certified that error appears in the above-identified patent and that said Letters Patent is hereby corrected as shown below:

On the title page, item 56

On page 2, in column 1, under "Other Publications", line 1, delete "mailed" and insert --filed--, therefor On page 2, in column 1, under "Other Publications", line 7, delete "mailed" and insert --filed--, therefor On page 2, in column 1, under "Other Publications", line 13, delete "2009"." and insert --2009", 7 pgs.--, therefor On page 2, in column 1, under "Other Publications", line 15, delete "2009"." and insert --2009", 7 pgs.--, therefor On page 2, in column 1, under "Other Publications", line 16, delete "C K," and insert --C. K.,--, therefor On page 2, in column 1, under "Other Publications", line 19, delete "AIP / Acoustical" and insert --AIP/Acoustical--, therefor On page 2, in column 2, under "Other Publications", line 3, delete "H," and insert --H.,--, therefor On page 2, in column 2, under "Other Publications", line 11-12, delete ""U.S. Appl. No. 12/102,602, Response filed to Restriction Requirement mailed Dec. 8, 2011", 8 pgs." and insert --"U.S. Appl. No. 12/102,602, Response filed Dec. 8, 2011 to Restriction Requirement mailed Nov. 8, 2011", 8 pgs.--, therefor On page 2, in column 2, under "Other Publications", line 33, delete "12/685,295 ," and insert --12/685,295,--, therefor Signed and Sealed this
Twenty-second Day of December, 2015

Michelle K. Lee
*Director of the United States Patent and Trademark Office*

CERTIFICATE OF CORRECTION (continued)
U.S. Pat. No. 8,571,224 B2

On the title page, item 56

On page 2, in column 2, under "Other Publications", line 35, delete "12/685,295 ," and insert --12/685,295,--, therefor On page 2, in column 2, under "Other Publications", line 41, delete "12/730,380 ," and insert --12/730,380,--, therefor On page 2, in column 2, under "Other Publications", line 56, delete "Filed" and insert --filed--, therefor On page 2, in column 2, under "Other Publications", line 58, delete "Filed" and insert --filed--, therefor On page 2, in column 2, under "Other Publications", line 58, delete "13." and insert --13 pgs.--, therefor On page 2, in column 2, under "Other Publications", line 70, delete "Mailed" and insert --mailed--, therefor On page 3, in column 1, under "Other Publications", line 2, delete "20 ," and insert --20,--, therefor On page 3, in column 2, under "Other Publications", line 7, delete "Dillon,Ph.D.," and insert --Dillon, Ph.D.,--, therefor On page 3, in column 2, under "Other Publications", line 9, delete "K" and insert --K.--, therefor On page 3, in column 2, under "Other Publications", line 13, delete "J," and insert --J.,--, therefor On page 3, in column 2, under "Other Publications", line 21, before "filed", insert --Application--, therefor In the claims In column 13, line 3, in Claim 6, before "tone", delete "test", therefor In column 13, line 6, in Claim 7, before "tone", delete "test", therefor In column 13, line 7, in Claim 7, before "tone", delete "test", therefor In column 14, line 2, in Claim 10, delete "distance, and" and insert --distance; and--, therefor